US008108053B2

(12) United States Patent
Zhao

(10) Patent No.: US 8,108,053 B2
(45) Date of Patent: Jan. 31, 2012

(54) SMALL CALIBER IMPLANTABLE BIOMETRIC LEADS AND CABLES FOR SAME

(75) Inventor: Yong D. Zhao, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 534 days.

(21) Appl. No.: 12/370,461

(22) Filed: Feb. 12, 2009

(65) Prior Publication Data

US 2010/0204767 A1 Aug. 12, 2010

(51) Int. Cl.
*A61N 1/00* (2006.01)
(52) U.S. Cl. ........................................... 607/122
(58) Field of Classification Search .................... 607/122
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 6,314,323 B1 | 11/2001 | Ekwall | |
| 7,366,556 B2 * | 4/2008 | Brister et al. | 600/347 |
| 2007/0106144 A1 | 5/2007 | Squeri | |
| 2009/0192577 A1 * | 7/2009 | Desai | 607/116 |

* cited by examiner

*Primary Examiner* — George Manuel

(57) ABSTRACT

Implantable medical leads have reduced diameter while providing for optimized mechanical and electrical properties, by reducing the diameters of the conducting cables used within the leads for sensing and delivery of therapeutic electrical stimulation. In an embodiment, conducting filaments within a cable have oval cross-sectional areas. Suitably orienting the oval filaments increases the contact surface between adjacent filaments, broadly distributing the pressure between filaments and reducing fretting fatigue, while the oval cross-sectional area also increases conductivity. In an embodiment, non-conducting coatings around filaments within a cable, or around groups of filaments organized into cable-layers, reduce fretting fatigue. In an embodiment, the cross-sectional area of filaments decreases as the filaments are positioned at increasing radial distances from the center of the cable. In an embodiment, the relative composition of various filament metals and/or alloys is varied in filaments at different radial distances from the center of the cable.

21 Claims, 26 Drawing Sheets

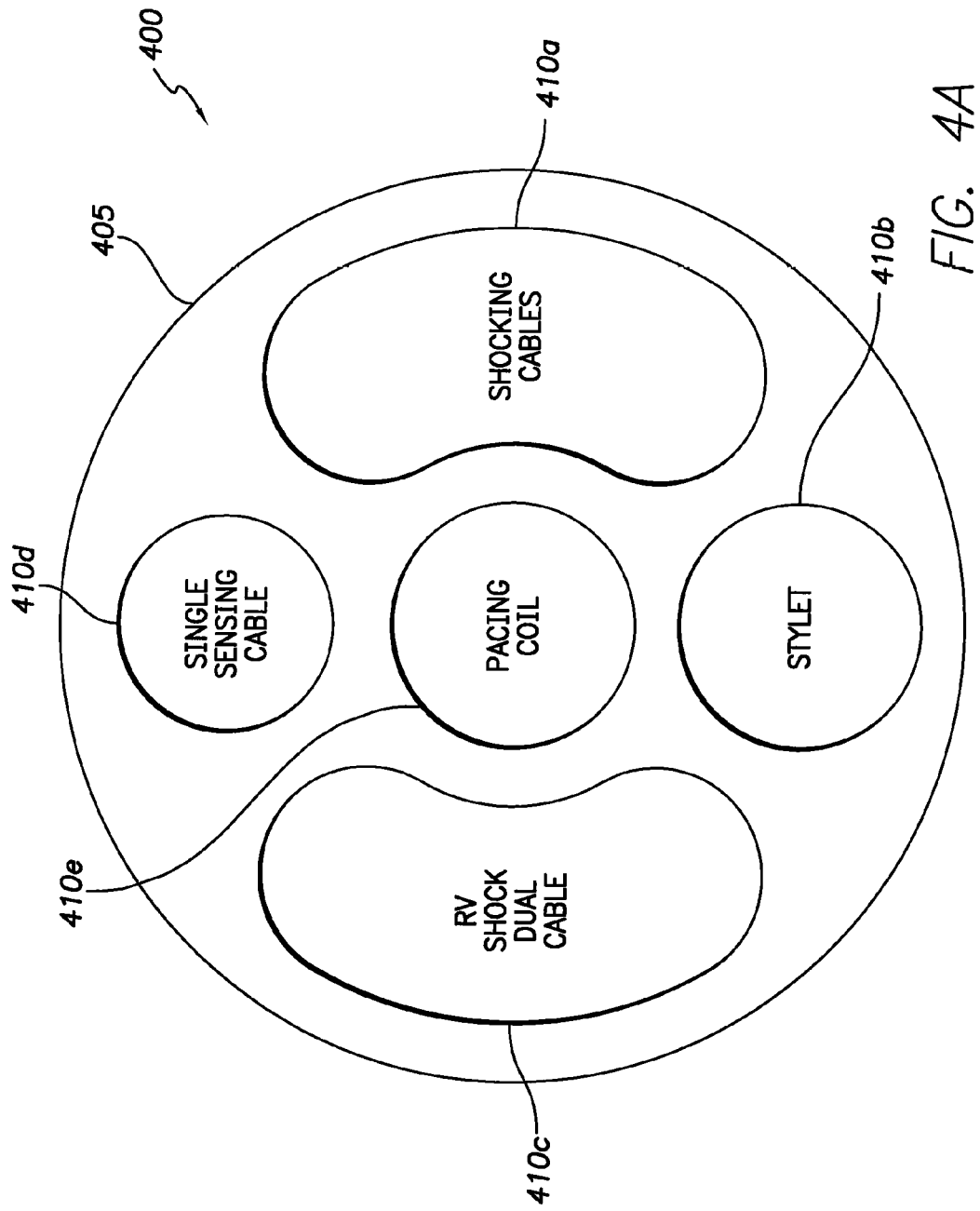

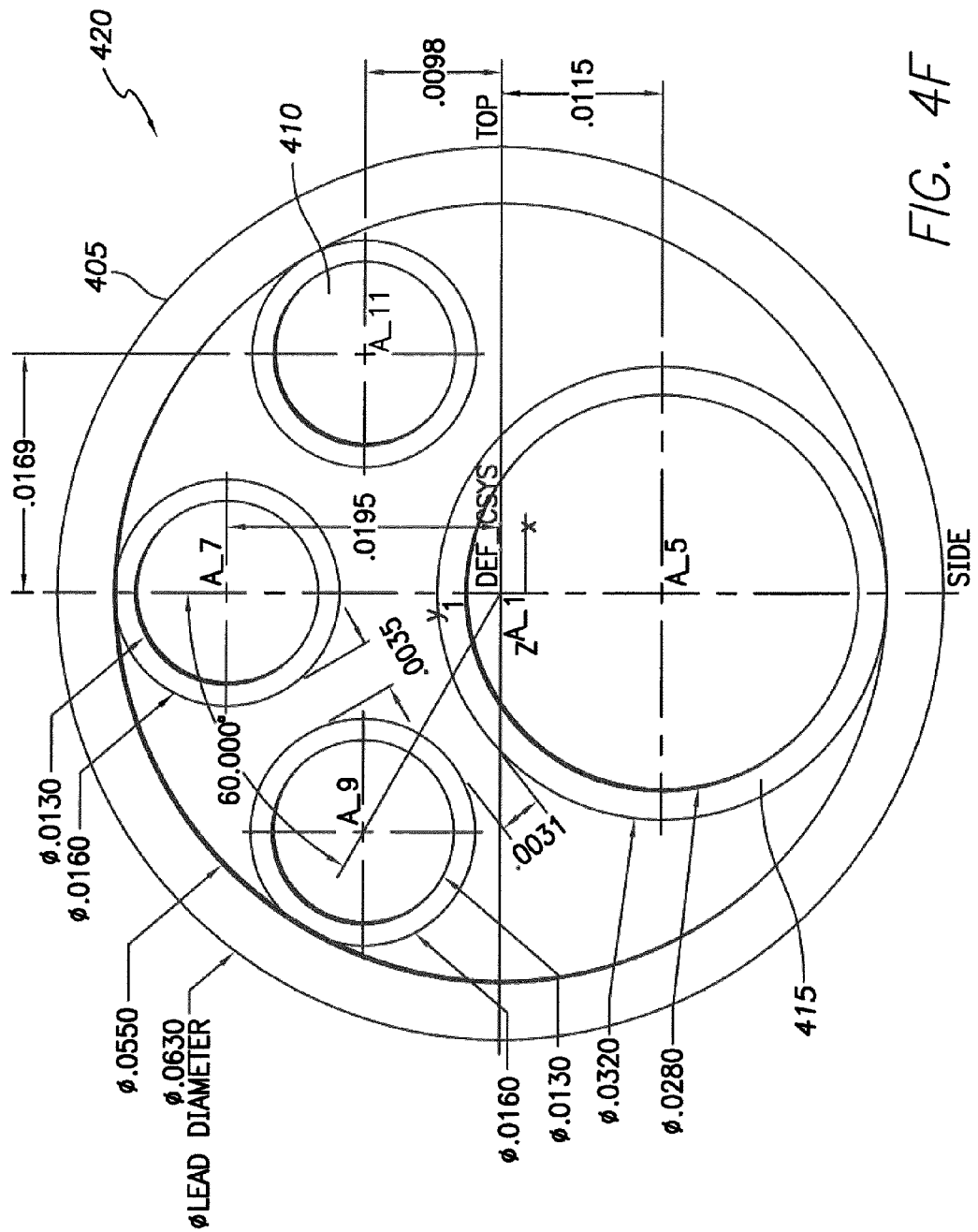

SMALL CALIBER IMPLANTABLE BIOMETRIC LEADS AND CABLES FOR SAME

FIELD OF THE INVENTION

The present invention relates generally to implantable cardiac therapy devices, and more specifically to implantable leads for implantable cardiac devices.

BACKGROUND

Implantable cardiac therapy devices (ICTDs) enjoy widespread use for providing convenient, portable, sustained therapy for cardiac patients with a variety of cardiac arrhythmias. ICTDs may combine a pacemaker and defibrillator in a single implantable device. Such devices may be configured to provide ongoing cardiac pacing in order to maintain an appropriate cardiac rhythm. In addition, should the ICTD detect that the patient is experiencing an episode of ventricular fibrillation (or an episode of ventricular tachycardia), the ICTD can deliver appropriate defibrillation therapy.

Cardiac rhythm management (CRM) therapies require not only an ICTD, but also the placement of electrical leads threaded through blood vessels and typically into the heart itself. Patients with implanted electrical leads benefit from leads which exhibit optimized properties in terms of size (that is, minimal lead width or diameter), flexibility, strength, and reliability (including resistance to breaking), and various electrical properties such as low impedance (in order to carry large current loads).

With advances in both CRM therapy and ICTD technologies, the device implant pathway can become busy with three or more cables (for example, cables may be required for treating bradycardia, tachycardia, defibrillation, cardiac pacing, for standalone sensors, etc.). These multiple leads may need to be placed inside only one or two veins, which in turn benefit from smaller size leads to ensure adequate circulation through the blood vessels. Adding new sensor based diagnostic features, such as LAP (left atrial pressure), RVP (right ventricular pressure), and SvO2 (blood oxygen sensor), requires creating additional space in the implant pathway or the lead body for the diagnostic circuits. Therefore, the addition of such sensors requires that the regular ICD lead diameter again must be reduced. Potential target drug delivery and target biological therapy delivery of tissues, cells, antibodies genes, etc. needs to be specifically delivered via a lead channel in the given vein with the new ICD leads. All of these therapeutic demands create requirements for the thinnest possible leads consistent with other lead requirements (flexibility, durability, low electrical resistance, and others).

With recent advances in cardiac therapies, alternative ICD lead implant sites are increasingly used. These include: the right ventricular outflow tract (ROT), the right ventricular (RV) high septum, and other sites in the right heart; and also the cardiac septum (CS), the great cardiac vein, and other areas of the left heart. To this end, the ICD leads must be robust and flexible for site specific positioning, and for ease of implantation through the torturous and complex implant pathways. ICTD leads also require improved acute and chronic stability at the desired site to reliably deliver the desired therapies for the entire design life of the system.

As is well known in the art, there are also different delivery methods to implant leads in the heart. The ICD lead should be compatible with traditional stylet delivery, and also be compatible with the emerging screw-driver stylet and/or slitable/steerable catheter, which benefits even more from a smaller size ICD lead.

Yet another aspect of lead design is enhanced lead removability, which becomes possible with leads that exhibit only minor fibrotic encapsulation. The degree of fibrosis engendered by a lead may be altered by optimized lead body materials and coatings, but here again a reduced electrical lead size contributes as well.

Yet another objective of lead design is MRI compatibility, which places specific requirements on the conductors for sizes, layout, insulation, etc.

The various operational requirements for ICTD leads, as specified above, create competing design requirements. In general, thinner leads contribute to flexibility and allow for maximum circulation within blood vessels. At the same time, it is known that fretting fatigue is the primary failure mode of a small-sized lead made of multiple filament wires; for example, the center filament wire is usually broken first in an existing 1×19 cable where all of the wires are of the same size. Further, smaller leads exhibit lower tensile strength. Also, when the lead size becomes smaller, the DC resistance of the cable increases, which in turn decreases the capability to carry large currents.

It will be noted that while implantable leads are essential in the field of cardiac rhythm management (CRM) therapies, they are employed in many other biomedical applications as well. For example, implantable leads have applications in neurology for treatment of Parkinson's disease, epilepsy, chronic back pain, and other conditions. Many of the requirements identified above, such as small size (i.e., being as thin as possible), flexibility, durability, and low resistance are requirements for these other applications as well.

What is needed, then, is an apparatus for an implantable lead for use with an ICTD, and for other implantable medical applications as well, with a smaller size lead which none-theless exhibits optimized performance for implantation in relation to existing leads including, for example:

flexible bending but higher tension strength;
    higher fatigue life;
    stronger ability to resist kinking;
    better electrical conductivity;
    lower DC resistance to carry large current during cardiac shocking.

BRIEF SUMMARY

The cable and lead designs presented herein show optimal mechanical and electrical performances especially for applications such as ICTD leads. The present cable and lead designs are directed towards reducing the diameter of leads, while providing for optimized mechanical and electrical properties, by reducing the diameters of the conducting cables used within the leads for both sensing and delivery of therapeutic electrical stimulation.

The diameter of the conducting cables may be reduced via multiple strategies. In an embodiment of the present cable and lead designs, conducting filaments within the lead are configured to have oval cross-sectional areas. By suitably orienting the oval filaments within a cable, it is possible to increase the contact surface between adjacent filaments. The increased contact surface area broadly distributes the pressure between filaments, resulting in reduced fretting fatigue. At the same time, the oval cross-sectional area increases conductivity and reduces DC resistance.

In an embodiment of the present cable and lead designs, suitable non-conductive coatings or jackets are employed around filaments within a cable, or around groups of filaments organized into cable-layers. The coatings or jackets reduce fretting fatigue, which enhances cable life and allows for the use of thinner filaments.

In an embodiment of the present cable and lead designs, the cross-sectional area of filaments used in a cable decreases as the filaments are positioned at increasing radial distance from the center of the cable. This configuration contributes to both structural strength and flexibility of the cable, while enabling a reduced cable diameter and maintaining optimized electrical properties.

In an embodiment of the present cable and lead designs, the relative composition of various metals and/or alloys of filaments in the cable is varied in relation to different radial distances of the filaments from the center of the cable. This configuration contributes both to structural strength and flexibility of the cables, while reducing cable diameter and maintaining optimized electrical properties.

Other and further features, advantages, and benefits of the present cable and lead designs will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate only several of many possible embodiments of the invention, and together with the description, serve to explain the principles of the invention in general terms.

BRIEF DESCRIPTION OF THE DRAWINGS/FIGURES

The accompanying drawings, which are incorporated herein and form part of the specification, illustrate the methods and systems presented herein for conductor cable designs for small caliber leads for an ICTD. Together with the detailed description, the drawings further serve to explain the principles of, and to enable a person skilled in the relevant art(s) to make and use the methods and systems presented herein.

In the drawings, like reference numbers indicate identical or functionally similar elements. Further, the drawing in which an element first appears is typically indicated by the leftmost digit(s) in the corresponding reference number (e.g., an element numbered 302 first appears in FIG. 3).

Additionally, some elements may be labeled with only a number to indicate a generic form of the element, while other elements labeled with the same number followed by another number or a letter (or a letter/number combination) may indicate a species of the element. For example, a generic filament of a cable may be labeled as 815. A filament associated specifically with an inner cable-layer may be labeled as 815.$i$, a filament associated with a middle cable-layer as 815.$m$, and a filament associated with an outer cable-layer as 815.$o$.

When referring to the figures, reference is sometimes made to a specific figure, for example, FIG. 5A, FIG. 5B, FIG. 6A, FIG. 10, etc. In other instances, especially where a group of figures illustrate different views and/or different sub-elements of a common element, reference may be made for convenience to the group of figures by way of a common figure number. For example, a reference to "FIG. 6" will be understood in this document as referring to all of, or to contextually pertinent aspects of, FIGS. 6A, 6B, 6C, 6D, and/or 6E as appropriate, as well as to the disclosure associated with those figures. A reference to "FIGS. 6-9" will be understood as referring to all of, or to contextually pertinent aspects of, FIGS. 6A-6E, 7A-7C, 8A, 8B, 9A, and 9B, as appropriate, as well as to the disclosure associated with those figures FIG. 1 is a simplified diagram illustrating an exemplary implantable cardiac therapy device (ICTD) in electrical communication with a patient's heart by means of leads suitable for delivering multi-chamber stimulation and pacing therapy, and for detecting cardiac electrical activity.

FIG. 4A illustrates a cross-sectional view of an exemplary implantable ICTD lead according to an embodiment of the present cable and lead designs.

FIG. 4F illustrates another view of the exemplary lead shown in FIG. 4E.

DETAILED DESCRIPTION

Overview

Figure 1:
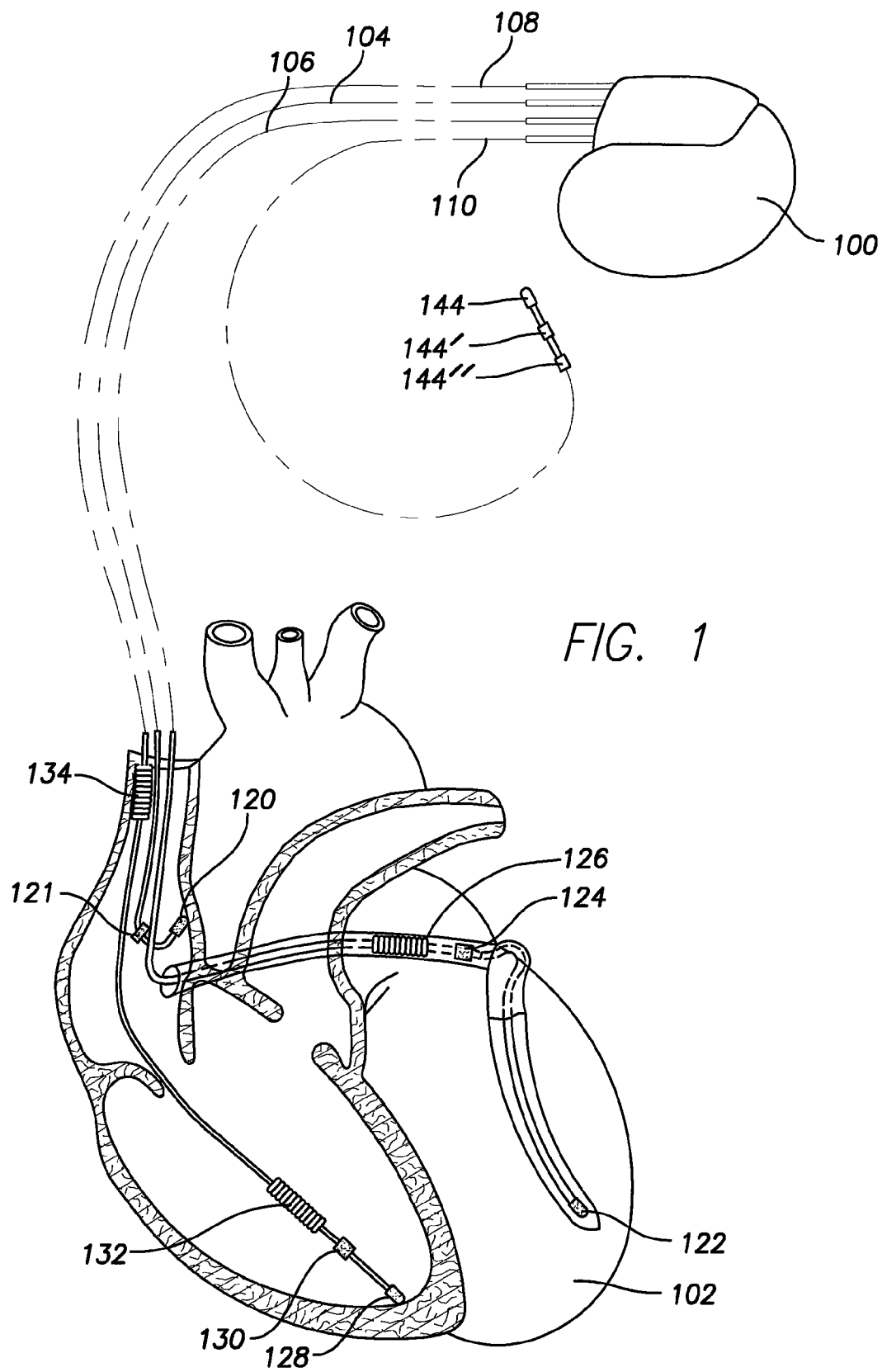

The following detailed description of systems and methods for conductor cable designs of small caliber ICTD leads for an implantable cardiac therapy device refers to the accompanying drawings that illustrate exemplary embodiments consistent with these systems and methods. Other embodiments are possible, and modifications may be made to the embodiments within the spirit and scope of the methods and systems presented herein. Therefore, the following detailed description is not meant to limit the methods and systems described herein. Rather, the scope of these methods and systems is defined by the appended claims.

It would be apparent to one of skill in the art that the systems and methods for conductor cable designs of small caliber ICTD leads for an implantable cardiac therapy device, as described below, may be implemented in many different embodiments of hardware, materials, construction methods, and/or the entities illustrated in the figures. Any actual hardware, materials, and/or construction methods described or illustrated herein is not limiting of these methods and systems. In addition, more than one embodiment of the present cable and lead designs may be presented below, and it will be understood that not all embodiments necessarily exhibit all elements, that some elements may be combined or connected in a manner different than that specifically described herein, and that some differing elements from the different embodiments presented herein may be functionally and structurally combined to achieve still further embodiments of the present cable and lead designs.

Thus, the operation and behavior of the methods and systems will be described with the understanding that modifications and variations of the embodiments are possible, given the level of detail presented herein.

It will be noted that while the exemplary embodiments presented below describe implantable leads, and cable conductors for use in the leads, used in the context of CRM therapies, the applications of the present cable and lead designs are not confined solely to leads employed for CRM therapies or to leads used in conjunction with ICTDs. For example, the exemplary leads described herein, and other similar leads falling within the scope of the appended claims, may be employed in other biomedical applications as well. For example, the implantable leads may have applications in neurology for treatment of Parkinson's disease, epilepsy, chronic back pain, etc. The leads may have other biomedical applications as well, and due to their various advantages, such as small size (i.e., being as thin as possible), flexibility, durability, and low resistance, and may even find beneficial applications in non-medical or non-biological applications as well.

Exemplary Environment—Overview

Before describing in detail the methods and systems for conductor cable designs of small caliber ICTD leads for an implantable cardiac therapy device, it is helpful to describe an example environment in which these methods and systems may be implemented. The methods and systems described herein may be particularly useful in the environment of an implantable cardiac therapy device (ICTD).

An ICTD may also be referred to synonymously herein as a "stimulation device", emphasizing the role of the ICTD in providing pacing and shocking to a human heart. However, an ICTD may provide operations or services in addition to stimulation, including but not limited to cardiac monitoring.

An ICTD is a physiologic measuring device and therapeutic device that is implanted in a patient to monitor cardiac function and to deliver appropriate electrical therapy, for example, pacing pulses, cardioverting and defibrillator pulses, and drug therapy, as required. ICTDs include, for example and without limitation, pacemakers, cardioverters, defibrillators, implantable cardioverter defibrillators, implantable cardiac rhythm management devices, and the like. Such devices may also be used in particular to monitor cardiac electrical activity and to analyze cardiac electrical activity. The term "implantable cardiac therapy device" or simply "ICTD" is used herein to refer to any such implantable cardiac device.

Figure 2:
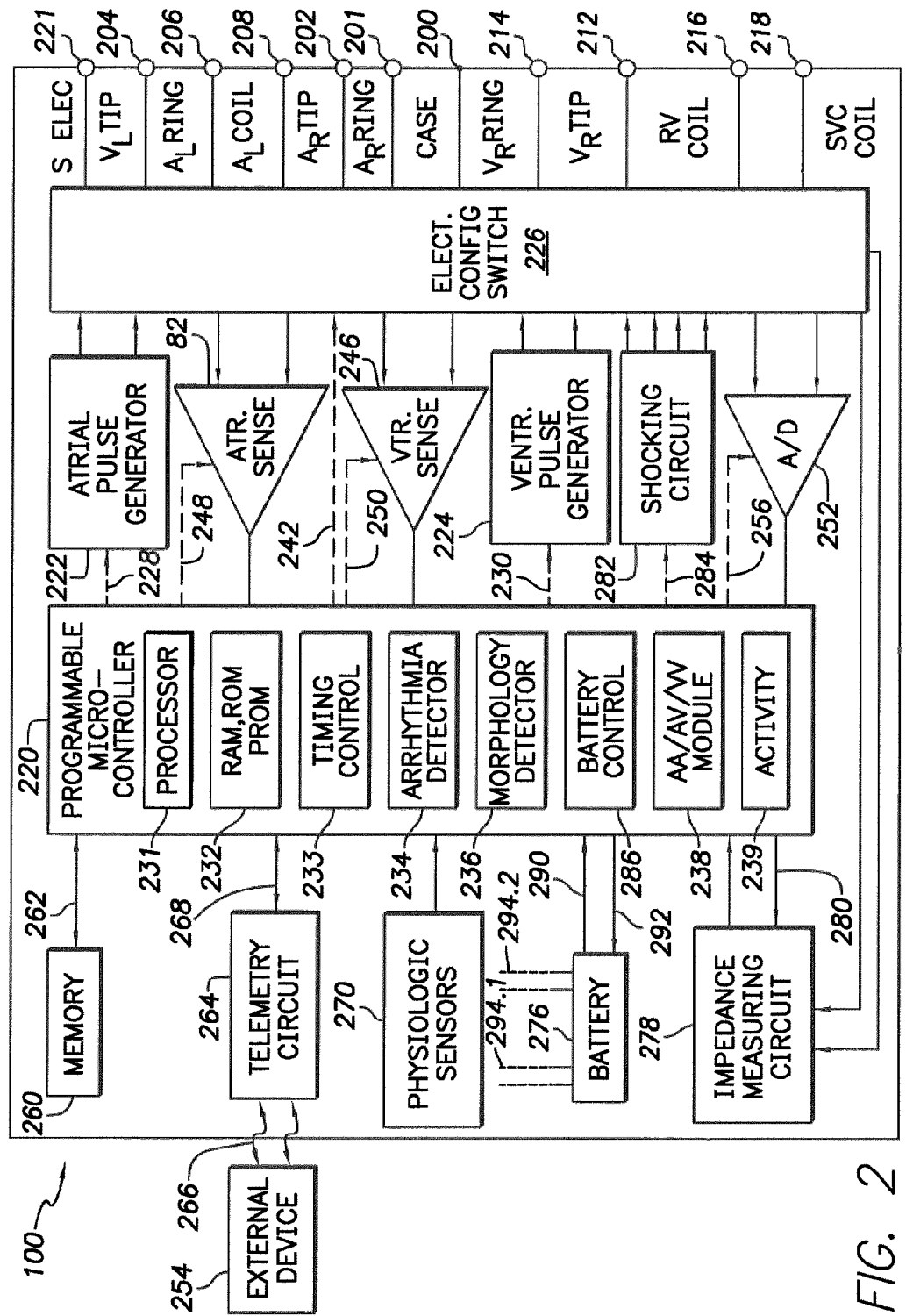
FIG. 2 is a functional block diagram of an exemplary ICTD that can detect cardiac electrical activity and analyze cardiac electrical activity, as well as provide cardioversion, defibrillation, and pacing stimulation in four chambers of a heart.

FIGS. 1 and 2 illustrate such an environment.
Exemplary ICTD in Electrical Communication with a Patient's Heart The techniques described below are intended to be implemented in connection with any ICTD or any similar stimulation device that is configured or configurable to stimulate nerves and/or stimulate and/or shock a patient's heart.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

As described further below in this document, exemplary leads 104, 106, 108, 110 have at least one interior electrically conducting cable, and may have multiple interior electrically conducting cables. The present cable and lead designs provide improved cable designs for use in leads such as exemplary leads 104, 106, 108, 110. Such improvements pertain to both mechanical and electrical properties of the cables, with resulting improvements in the mechanical and electrical properties of leads 104, 106, 108, 110.

Figure 4B:
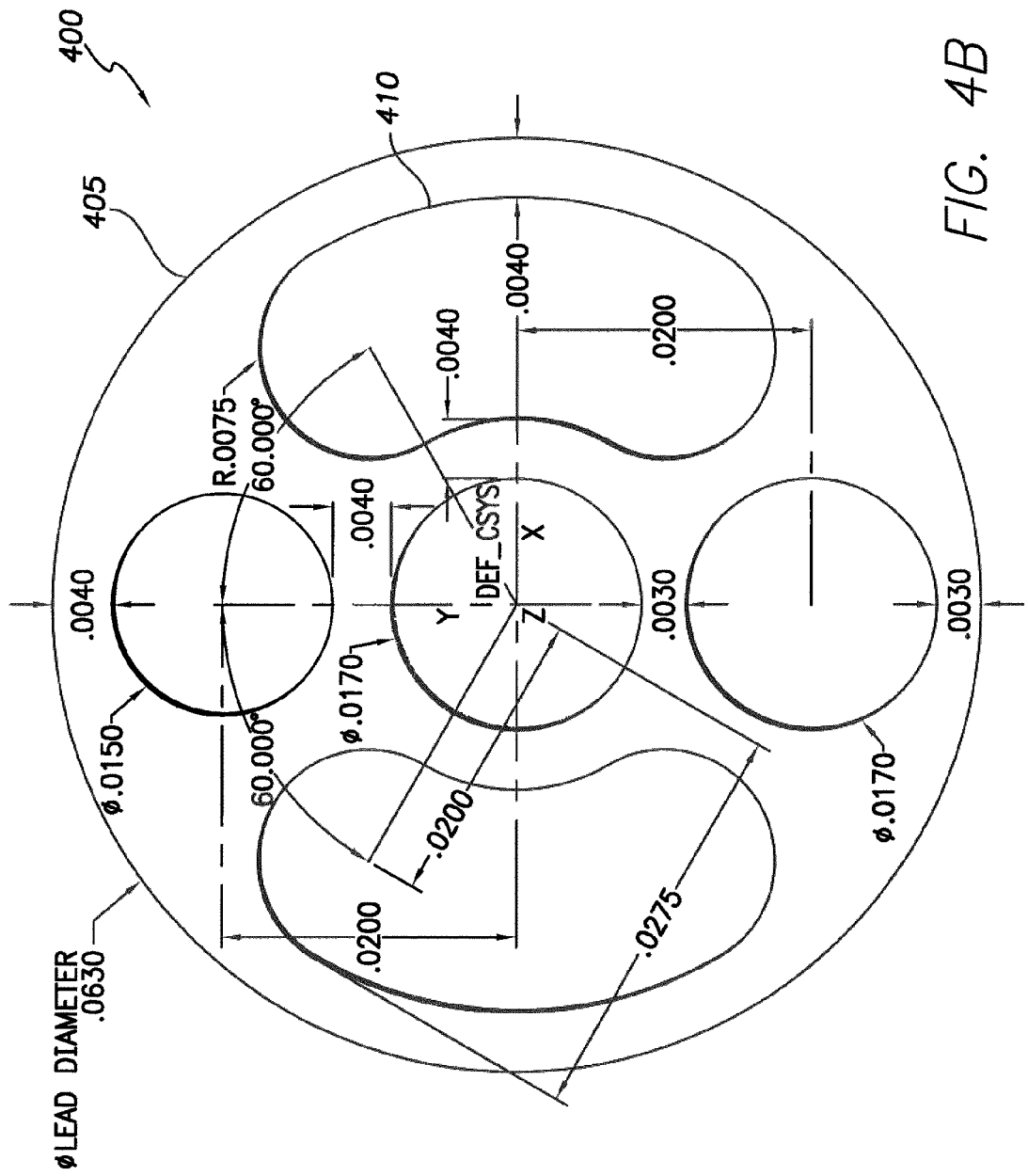
FIG. 4B illustrates another cross-sectional view of the exemplary lead shown in FIG. 4A.
Figure 4C:
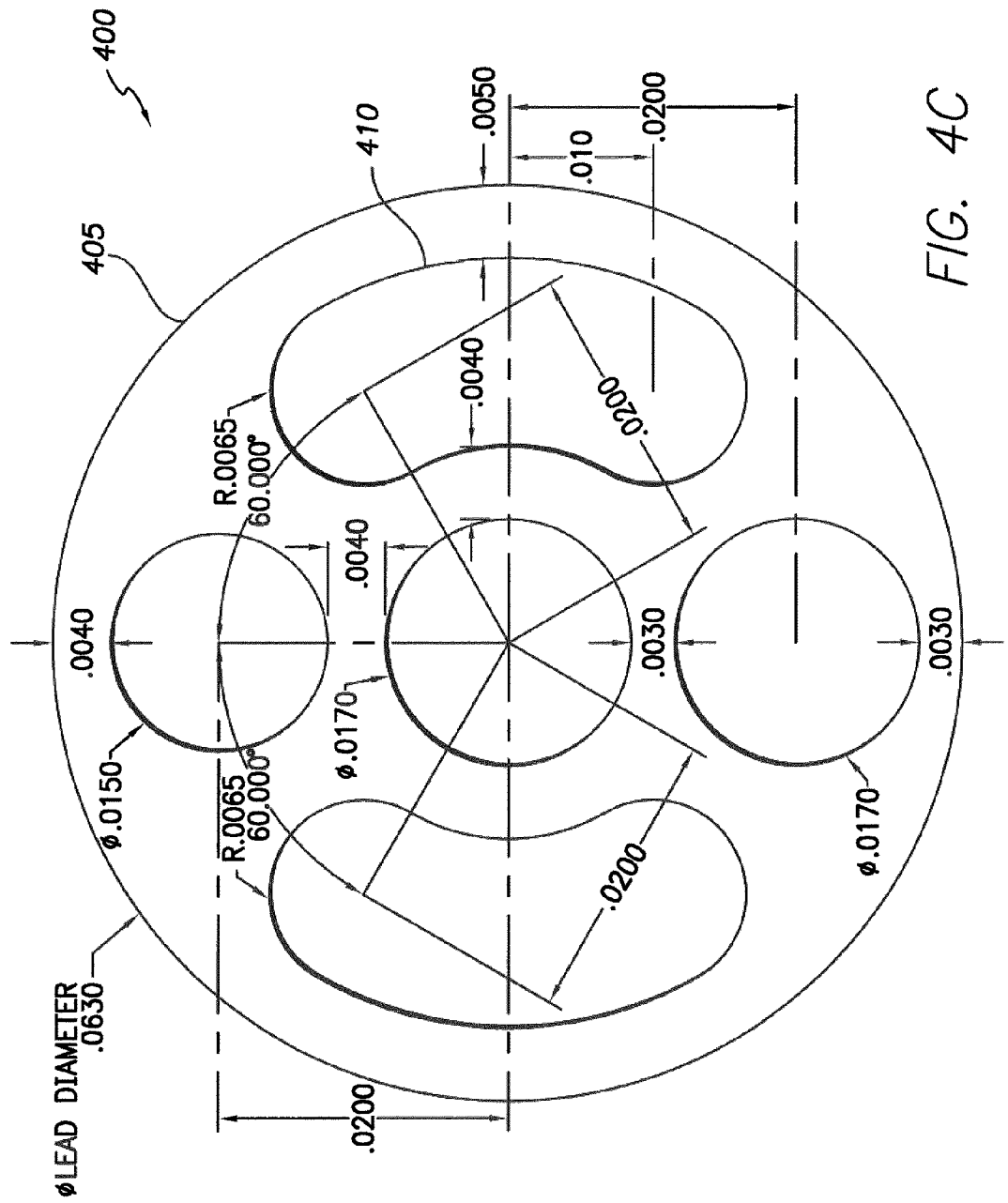
FIG. 4C illustrates another cross-sectional view of the exemplary lead shown in FIG. 4A with a different set of dimensions than those shown in FIG. 4B.
Figure 4D:
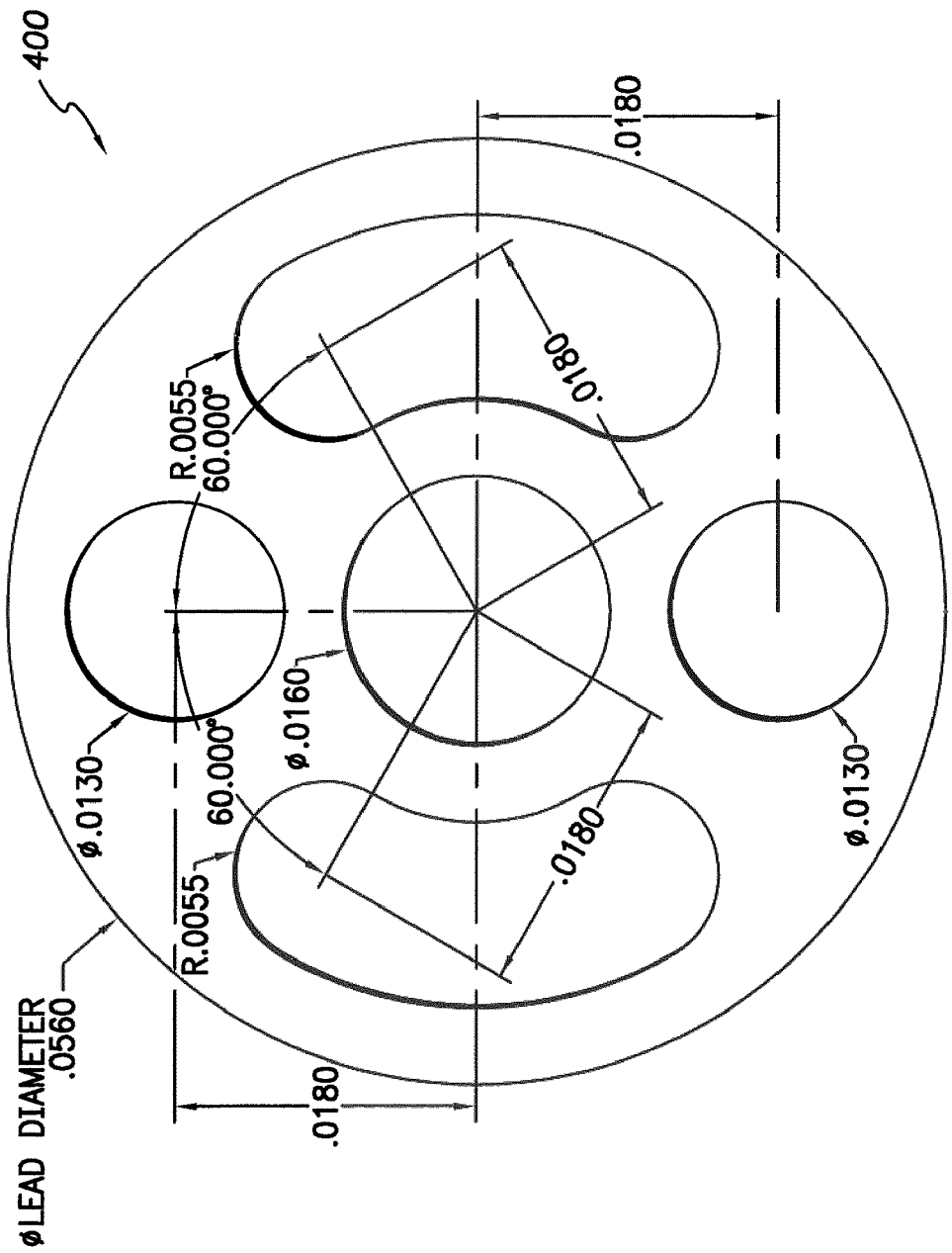
FIG. 4D illustrates another cross-sectional view of the exemplary lead shown in FIG. 4A with a different set of dimensions than those shown in FIG. 4B or FIG. 4C.
Figure 4E:
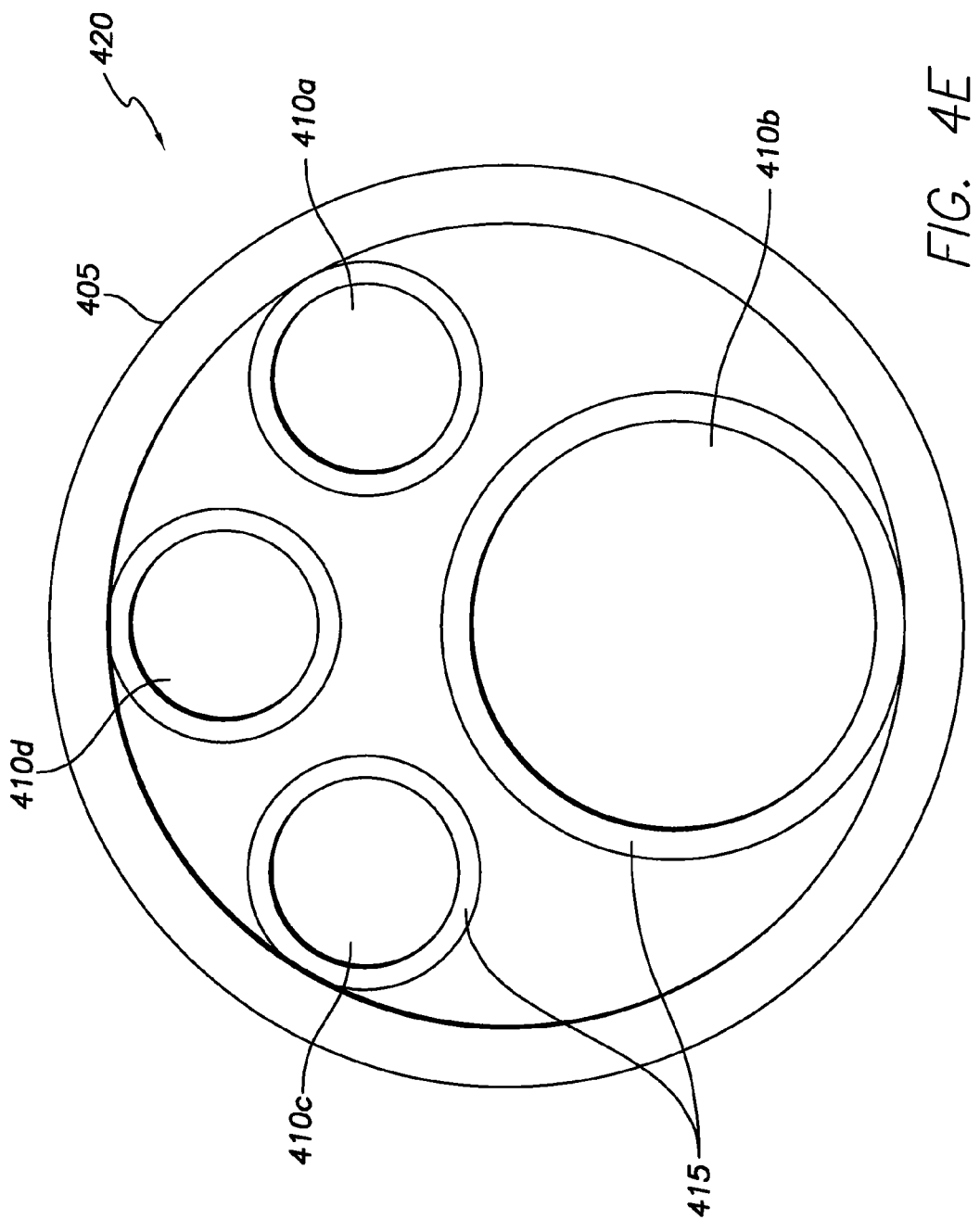
FIG. 4E illustrates a cross-sectional view of another exemplary implantable ICTD lead according to the present cable and lead designs.
Figure 5A:
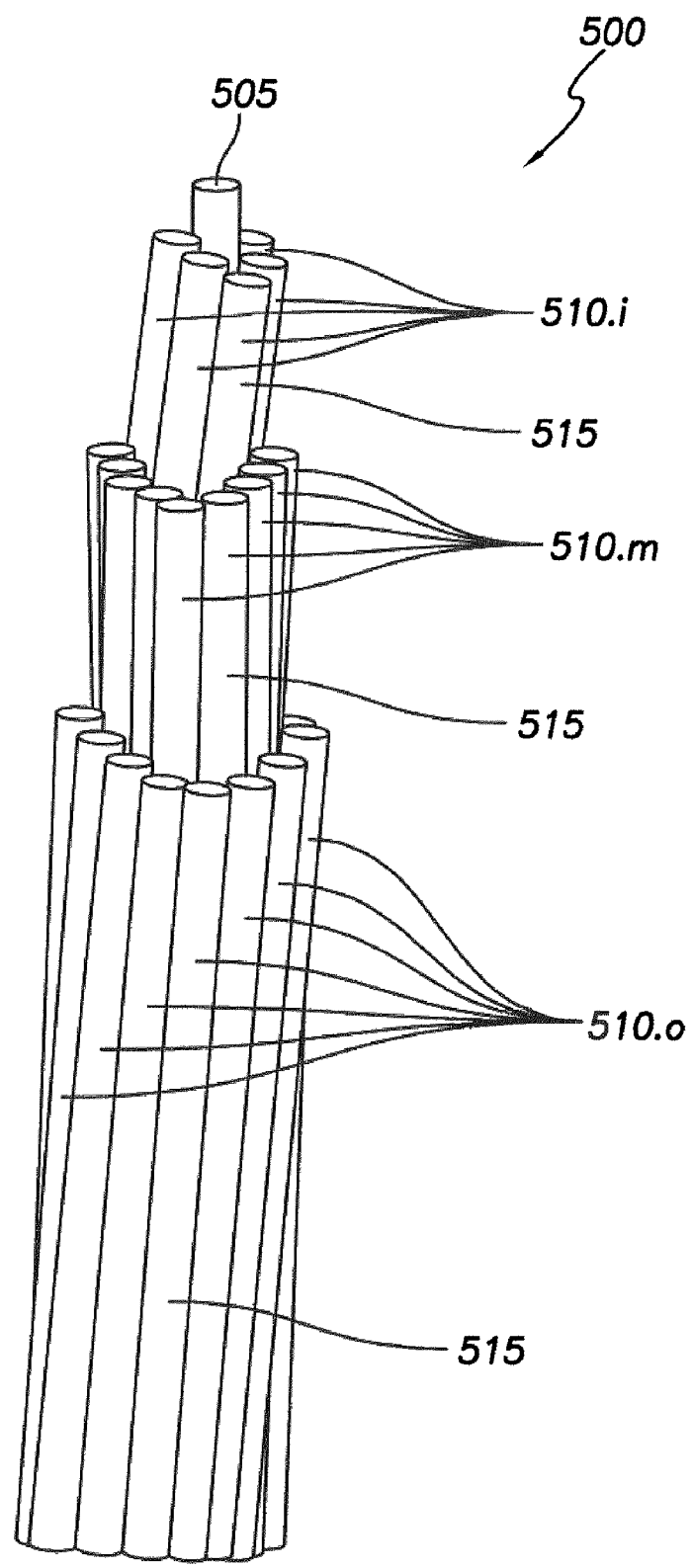
FIG. 5A illustrates an exemplary cable which may be part of a lead.

General background information on cable designs is provided in FIGS. 5A-5D along with the associated description, with discussion of some of the advantages of the present cable and lead designs being presented in conjunction with FIG. 5F. The present lead and cable designs are described in further detail later in this document, particularly but not exclusively in the section of this document titled "Cable Designs Overview;" and also with reference to exemplary leads 400 and 420 illustrated in FIGS. 4A-4F; exemplary cable conductors 600, 700, 800, and 900 illustrated in FIGS. 6-9; and exemplary central wires 605, 705, 805, 905 and exemplary filaments 615, 715, 815, 915 illustrated in various illustrations of FIGS. 6-10. It will be understood by persons skilled in the relevant arts that leads 104, 106, 108, 110 and other leads used in conjunction with operations of ICTD 100 may employ designs the same as or similar to exemplary leads 400, 420; and may further employ conducting cables, central wires, and filaments the same as, or embodying elements of, exemplary cable conductors 600, 700, 800, and 900, exemplary central wires 605, 705, 805, 905, and exemplary filaments 615, 715, 815, 915, as described further below in this document.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Functional Elements of an Exemplary ICTD

An implantable cardiac therapy device may be referred to variously, and equivalently, throughout this document as an "implantable cardiac therapy device", an "ICTD", an "implantable device", a "stimulation device", and the respective plurals thereof.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126,132 and 134 (see FIG. 1) for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, shocking, and/or autonomic stimulation, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a processor or microprocessor 231, or equivalent control circuitry, designed specifically for controlling the delivery of stimulation therapy, and may further include onboard memory 232 (which may be, for example and without limitation, RAM, ROM, PROM, one or more internal registers, etc.), logic and timing circuitry, state machine circuitry, and I/O circuitry.

Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 233 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module (the latter two are not shown in FIG. 2). These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. Such a module may help make determinations as to fusion.

The microcontroller 220 of FIG. 2 also includes an activity module 239. This module may include control logic for one or more activity related features. For example, the module 239 may include an algorithm for determining patient activity level, calling for an activity test, calling for a change in one or more pacing parameters, etc. These algorithms are described in more detail with respect to the figures. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

Microcontroller 220 may also include a battery control module 286. Battery control module 286 may be used, for example, to control a battery 276. Battery control 286 may be hardwired circuitry, or may be implemented as software or firmware running on microcontroller 220. Battery control 286 may be coupled to battery 276 via battery signal line 290 and battery control line 292. Battery signal line 290 may deliver to battery control 286 status or operational information regarding battery 276. Battery control line 292 may be used to change an operational state of battery 276. For example, battery control line 292 may deliver control signals from battery control 286 to battery 276.

In an alternative embodiment, battery control 286 may be a separate module from microcontroller 220, but may be coupled to microcontroller 220. For example, separate module battery control 286 may obtain required ICTD operational status information from microcontroller 220. Or, for example, separate module battery control 286 may report battery status or battery operational information to microcontroller 220. In addition, separate module battery control 286 may also be coupled to battery 276.

In an alternative embodiment, battery control 286 may be implemented as an internal physical module of battery 276 (for example, battery control 286 may be implemented as a microchip which is situated internally to the exterior housing of battery 276). However, battery control 286 may still be coupled to microcontroller 220 via battery signal line 290 and battery control line 292. In an alternative embodiment, battery control functions of battery control 286 may be distributed across a first module which is part of battery 276, and one or more additional modules which are external to battery 276. The battery control module(s) external to battery 276 may for example be part of microcontroller 220.

The electrode configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart.

Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the analog-to-digital (A/D) data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram (EGM) signals, convert the raw analog data into a digital signal, and store the digital signals for later processing and/or telemetric transmission to an external device 254. Data acquisition system 252 may be configured by microcontroller 220 via control signals 256. The data acquisition system 252 is coupled to the right atrial lead 104, the coronary sinus lead 106, the right ventricular lead 108 and/or the nerve stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature may be the ability to sense and store a relatively large amount of data (e.g., from the data acquisition system 252), which data may then be used for subsequent analysis to guide the programming of the device.

Essentially, the operation of the ICTD control circuitry, including but not limited to pulse generators, timing control circuitry, delay modules, the activity module, battery utilization and related voltage and current control, and sensing and detection circuits, may be controlled, partly controlled, or fine-tuned by a variety of parameters, such as those indicated above which may be stored and modified, and may be set via an external ICTD programming device.

Advantageously, the operating parameters of the implantable device 100 may be non-invasively programmed into the memory 260 through a telemetry circuit 264 in telemetric communication via communication link 266 with the external device 254, such as a general purpose computer, a dedicated ICTD programmer, a transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266. The ICTD 100 may also receive human programmer instructions via the external device 254.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 may respond by adjusting the various pacing parameters (such as rate, AA delay, AV delay, W delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of an example activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2, as well as to any additional circuits which may be present in alternative embodiments. Operating power in the form of electrical current and/or voltage may be provided via a power bus or power buses 294, depicted in FIG. 2 as a first power bus 294.1 and a second power bus 294.2. In FIG. 2, the connection(s) of power bus(es) 294 to other elements of ICTD 100 for purposes of powering those elements is not illustrated, but is implied by the dotted end-lines of bus(es) 294.

For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 Amps, at voltages above 2 volts, for periods of 10 seconds or more). In an embodiment, battery 276 may be configured to provide a current as high as 3.5 to 4.5 Amps and/or unloaded voltages in excess of 4 volts, for rapid charging of shocking circuitry. Battery 276 also desirably has a predictable discharge characteristic so that elective replacement time can be determined.

In an embodiment, battery 276 may be a hybrid battery comprised of dual types of cells. Such a hybrid battery may provide power via a plurality of power buses, such as buses 249.1 and 294.2 of FIG. 2. In an embodiment, each power bus may be configured to deliver different voltages, different currents, and/or different power levels. Battery 276 may be monitored and/or controlled via battery control 286, as discussed in part above, and as also discussed further below.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuit 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICTD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Shocking circuit 282 either has within it, or is coupled to, one or more shocking capacitors (not shown in FIG. 2). The shocking capacitor(s) may be used to store up energy, and then release that energy, during the generation of shocking pulses.

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, microcontroller 220 is capable of controlling the synchronous or asynchronous delivery of the shocking pulses.

ICTD Programmer

As indicated above, the operating parameters of the implantable device 100 may be non-invasively programmed into the memory 260 through a telemetry circuit 264 in telemetric communication via communication link 266 with the external device 254. The external device 254 may be a general purpose computer running custom software for programming the ICTD 100, a dedicated external programmer device of ICTD 100, a transtelephonic transceiver, or a diagnostic system analyzer. Generically, all such devices may be understood as embodying computers, computational devices, or computational systems with supporting hardware or software which enable interaction with, data reception from, and programming of ICTD 100.

Throughout this document, where a person is intended to program or monitor ICTD 100 (where such person is typically a physician or other medical professional or clinician), the person is always referred to as a "human programmer" or as a "user". The term "human programmer" may be viewed as synonymous with "a person who is a user of an ICTD programming device", or simply with a "user". Any other reference to "programmer" or similar terms, such as "ICTD programmer", "external programmer", "programming device", etc., refers specifically to the hardware, firmware, software, and/or physical communications links used to interface with and program ICTD 100.

The terms "computer program", "computer code", and "computer control logic" are generally used synonymously and interchangeably in this document to refer to the instructions or code which control the behavior of a computational system. The term "software" may be employed as well, it being understood however that the associated code may in some embodiments be implemented via firmware or hardware, rather than as software in the strict sense of the term (e.g., as computer code stored on a removable medium, or transferred via a network connection, etc.).

A "computer program product" or "computational system program product" is a medium (for example, a magnetic disk drive, magnetic tape, optical disk (e.g., CD, DVD), firmware, ROM, PROM, flash memory, a network connection to a server from which software may be downloaded, etc) which is suitable for use in a computer or computation system, or suitable for input into a computer or computational system, where the medium has control logic stored therein for causing a processor of the computational system to execute computer code or a computer program. Such medium, also referred to as "computer program medium", "computer usable medium", and "computational system usable medium", are discussed further below.

Figure 3:
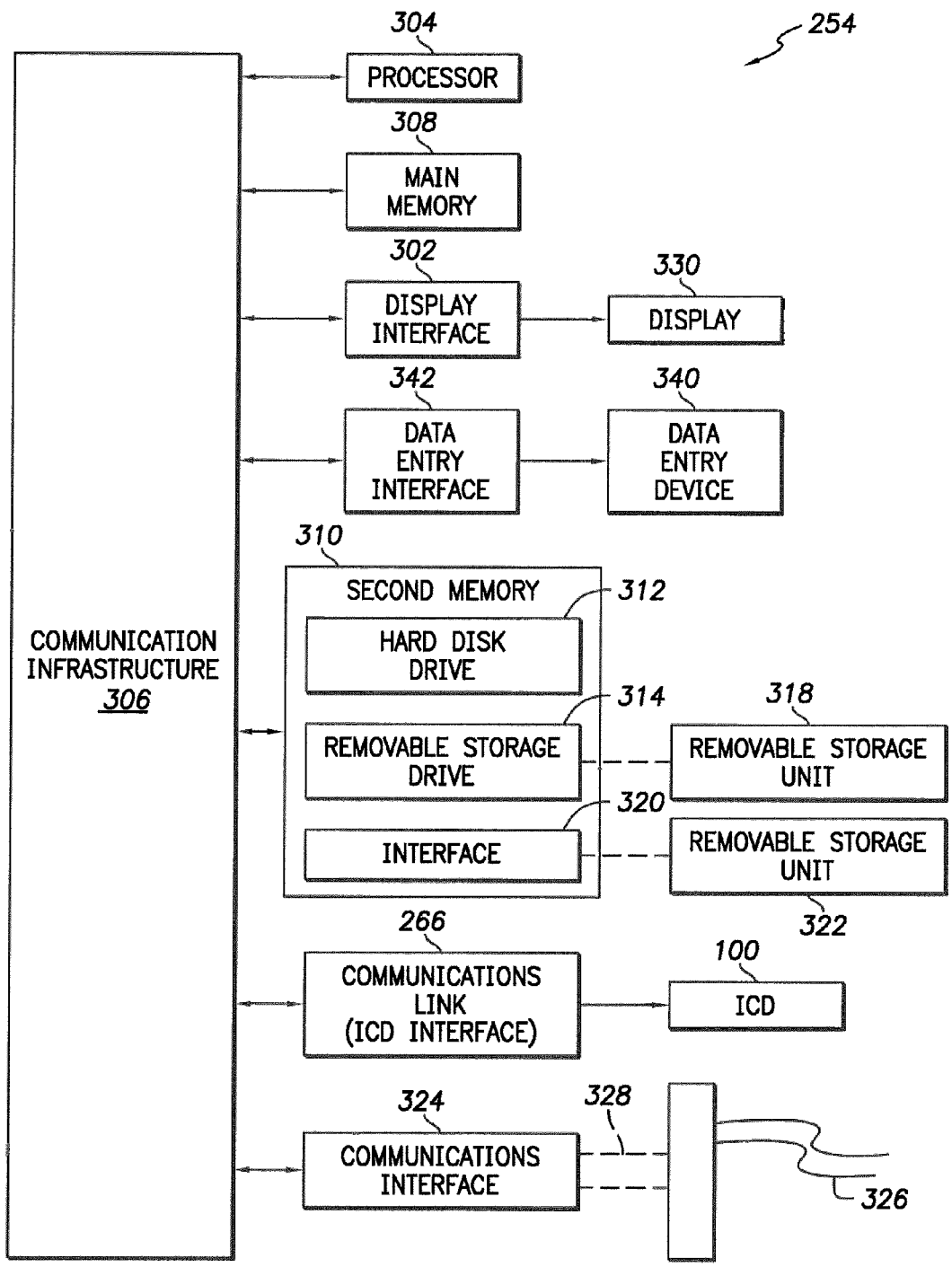
FIG. 3 is a system diagram representing an exemplary computer, computational system, or other programming device which may be used to program an ICTD.

FIG. 3 presents a system diagram representing an exemplary computer, computational system, or other programming device, which will be referred to for convenience as ICTD programmer 254. It will be understood that while the device is referred to an "ICTD programmer", indicating that the device may send programming data, programming instructions, programming code, and/or programming parameters to ICTD 100, the ICTD programmer 254 may receive data from ICTD 100 as well, and may display the received data in a variety of formats, analyze the received data, store the received data in a variety of formats, transmit the received data to other computer systems or technologies, and perform other tasks related to operational and/or physiologic data received from ICTD 100.

ICTD programmer 254 includes one or more processors, such as processor 304. Processor 304 is used for standard computational tasks well known in the art, such as retrieving instructions from a memory, processing the instructions, receiving data from memory, performing calculations and analyses on the data in accordance with the previously indicated instructions, storing the results of calculations back to memory, programming other internal devices within ICTD programmer 254, and transmitting data to and receiving data from various external devices such as ICTD 100.

Processor 304 is connected to a communication infrastructure 306 which is typically an internal communications bus of ICTD programmer 254; however, if ICTD programmer 254 is implemented in whole or in part as a distributed system, communication infrastructure 306 may further include or may be a network connection.

ICTD programmer 254 may include a display interface 302 that forwards graphics, text, and other data from the communication infrastructure 306 (or from a frame buffer not shown) for display on a display unit 330. The display unit may be, for example, a CRT, an LCD, or some other display device. Display unit 330 may also be more generally understood as any device which may convey data to a human programmer.

Display unit 330 may also be used to present a user interface which displays internal features of, operating modes or parameters of, or data from ICTD 100. The user interface presented via display unit 330 of ICTD programmer 254 may include various options that may be selected, deselected, or otherwise changed or modified by a human programmer of ICTD 100. The options for programming the ICTD 100 may be presented to the human programmer via the user interface in the form of buttons, check boxes, menu options, dialog boxes, text entry fields, or other icons or means of visual display well known in the art.

ICTD programmer 254 may include a data entry interface 342 that accepts data entry from a human programmer via data entry devices 340. Such data entry devices 340 may include, for example and without limitation, a keyboard, a mouse, a touchpad, a touch-sensitive screen, a microphone for voice input, or other means of data entry, which the human programmer uses in conjunction with display unit 330 in a manner well known in the art. For example, either a mouse or keystrokes entered on a keyboard may be used to select check boxes, option buttons, menu items, or other display elements indicating human programmer choices for programming ICTD 100. Direct text entry may be employed as well. Data entry device 340 may also take other forms, such as a dedicated control panel with specialized buttons and/or other mechanical elements or tactile sensitive elements for programming ICTD 100.

Display interface 302 may present on display unit 330 a variety of data related to patient cardiac function and performance, and also data related to the present operating mode, operational state, or operating parameters of ICTD 100. Modifications to ICTD 100 operational state(s) may be accepted via data entry interface 342 and data entry device 340. In general, any interface means which enables a human programmer to interact with and program ICTD 100 may be employed. In one embodiment, for example, a visual data display may be combined with tactile data entry via a touchscreen display.

In another embodiment, a system of auditory output (such as a speaker or headset and suitable output port for same, not shown) may be employed to output data relayed from ICTD 100, and a system of verbal input (such as a microphone and suitable microphone port, not shown) may be employed to program ICTD 100. Other modes of input and output means may be employed as well including, for example and without limitation, a remote interaction with ICTD 100, viewing printed data which has been downloaded from ICTD 100, or the programming of ICTD 100 via a previously coded program script.

All such means of receiving data from ICTD 100 and/or programming ICTD 100 constitute an interface 302, 330, 342, 340 between ICTD 100 and a human programmer of ICTD 100, where the interface is enabled via both the input/output hardware (e.g., display screen, mouse, keyboard, touchscreen, speakers, microphone, input/output ports, etc.) and the hardware, firmware, and/or software of ICTD programmer 254.

ICTD programmer 254 also includes a main memory 308, preferably random access memory (RAM), and may also include a secondary memory 310. The secondary memory 310 may include, for example, a hard disk drive 312 and/or a removable storage drive 314, representing a floppy disk drive, a magnetic tape drive, an optical disk drive, etc. The removable storage drive 314 reads from and/or writes to a removable storage unit 318 in a well known manner. Removable storage unit 318 represents a magnetic disk, magnetic tape, optical disk, etc. which is read by and written to by removable storage drive 314. As will be appreciated, the removable storage unit 318 includes a computer usable storage medium having stored therein computer software and/or data.

In alternative embodiments, secondary memory 310 may include other similar devices for allowing computer programs or other instructions to be loaded into ICTD programmer 254. Such devices may include, for example, a removable storage unit 322 and an interface 320. Examples of such may include a program cartridge and cartridge interface (such as that found in video game devices), a removable memory chip (such as an erasable programmable read only memory (EPROM), programmable read only memory (PROM), or flash memory) and associated socket, and other removable storage units 322 and interfaces 320, which allow software and data to be transferred from the removable storage unit 322 to ICTD programmer 254.

ICTD programmer 254 also contains a communications link 266 to ICTD 100, which may be comprised in part of a dedicated port of ICTD programmer 254. From the perspective of ICTD programmer 254, communications link 266 may also be viewed as an ICTD interface. Communications link 266 enables two-way communications of data between ICTD programmer 254 and ICTD 100. Communications link 266 has been discussed above (see the discussion of FIG. 2A).

ICTD programmer 254 may also include a communications interface 324. Communications interface 324 allows software and data to be transferred between ICTD programmer 254 and other external devices (apart from ICTD 100). Examples of communications interface 324 may include a modem, a network interface (such as an Ethernet card), a communications port, a Personal Computer Memory Card International Association (PCMCIA) slot and card, a USB port, an IEEE 1394 (FireWire) port, etc. Software and data transferred via communications interface 324 are in the form of signals 328 which may be electronic, electromagnetic, optical (e.g., infrared) or other signals capable of being received by communications interface 324. These signals 328 are provided to communications interface 324 via a communications path (e.g., channel) 326. This channel 326 carries signals 328 and may be implemented using wire or cable, fiber optics, a telephone line, a cellular link, an radio frequency (RF) link, in infrared link, and other communications channels.

The terms "computer program medium", "computer usable medium", and "computational system usable medium" are used, synonymously, to generally refer to media such as removable storage drive 314 and removable storage unit 381, a hard disk installed in hard disk drive 312, a secondary memory interface (such as a flash memory port, USB port, FireWire port, etc.) and removable storage unit 322 (such as flash memory), and removable storage units 318 and 322. These computer program products or computational system program products provide software to ICTD programmer 254.

It should be noted, however, that it is not necessarily the case that the necessary software, computer code, or computer program (any of which may also referred to as computer control logic) be loaded into ICTD programmer 254 via a removable storage medium. Such computer program may be loaded into ICTD programmer 254 via communications link 328, or may be stored in memory 308 of ICTD programmer 254. Computer programs are stored in main memory 308 and/or secondary memory 310. Computer programs may also be received via communications interface 324.

Accordingly, such computer programs represent controllers of ICTD programmer 254, and thereby controllers of ICTD 100. Software may be stored in a computer program product and loaded into ICTD programmer 254 using removable storage drive 314, hard drive 312, secondary memory interface 320, or communications interface 324.

DEFINITIONS

Below are definitions of some of the terms employed in this document.

It should be understood that various terms, such as "lead," "cable," "conductor," "filament," "wire," "cable-layer," and similar terms may be used or employed variously among persons skilled in the relevant arts. Related, similar, or partially similar elements used elsewhere in the art may be named or described differently and with different terms in other documents.

Lead: Also known as a cardiac lead. An elongated, flexible tubular element, commonly though not necessarily with a circular cross-section orthogonal to the axis of elongation. A lead is composed of one or more cables, and a sheath which houses the cables, as defined further below. A lead has a proximal end and a distal end. The proximal end of the lead is designed to attach to an ICTD or other therapeutic or sensing device. The distal end of the lead is designed to have one or more elements for attaching the lead to organic tissue (e.g., fixing tines), and/or electrode elements for delivery of electricity to organic tissue (typically for therapeutic purposes), and/or other elements for delivery of other therapeutic treatments to organic tissue, and/or elements for sensing an activity of organic tissue.

In some cases, the attaching element(s) may be the same as the electrode(s), other therapeutic delivery element(s), or sensing element(s). In some cases, elements for attaching to organic tissue, for delivery of electricity, for delivery of other therapeutic treatments, or for sensing may also be placed at one or more points intermediate between the proximal end and the distal end. Suitable alterations, such as placement of punctures or holes, made be made to the sheath (defined below) and to other jacketing, coating, or insulation (defined below) to enable suitable mechanical and/or electrical connectivity between these intermediate elements and the interior electrically conducting cables and/or other interior therapeutic delivery pathways of the lead. Exemplary leads are illustrated in FIGS. 4, discussed below.

Sheath: The body is a typically non-conducting element of a lead which provides the exterior insulation of the lead and may also provide interior separation and/or insulation between two or more conducting cables (as defined below) if multiple cables are employed within the lead. The sheath typically extends the full length or almost the full length of the lead, possibly excluding the length of the proximal and distal end elements (for attaching to the ICTD, end electrodes, etc.) As will be understood by persons skilled in the relevant arts, the sheath of a lead may have multiple layers, for example an inner insulating sheath and an outermost sheath. The sheath may be made from any number of materials which demonstrate resilience and flexibility including, for example and without limitation, silicone rubber, polyurethane, Optim® (a silicone-polyurethane co-polymer insulation), PTFE (polytetrafluoroethylene), or ETFE (ethylene-tetrafluoroethylene), polyimide, paryline, PFA, etc. Exemplary sheaths are illustrated in FIGS. 4, discussed below.

Lumen: The sheath provides one or more hollow, mutually insulated interior canals or tubular spaces known as "lumens," running substantially parallel to the outer wall of the sheath, which typically run the full length of the sheath. The lumens are designed to provide a pathway for one or more electrically conducting cables and/or coil conductors for delivery of therapeutic treatments or for sensing, or pathways for delivery of other therapeutic treatments. One or more lumens may also be designed to accommodate a stylet or wire guide, etc. Exemplary lumens are illustrated in FIGS. 4, discussed below.

Multilumen: When an element has two or more lumens running through it, these may be referred to together as a multilumen. In this document, the term "lumen" may sometimes be used in place of "multilumen" where the context makes clear the meaning, or where either a lumen (single canal) or multilumen may be intended.

Cable: A cable is an electrically conducting element made from a conducting material (including for example and without limitation silver, copper, nickel, chromium, aluminum, iron, molybdenum, etc., and/or various alloys of these metals and other metals), typically running the full length or substantially the full length of an ICTD lead. The conducting elements of a cable (central core, cable-layers, and filaments, defined further below) are also composed of conducting elements (including for example and without limitation silver, copper, nickel, chromium, aluminum, iron, molybdenum, etc., and/or various alloys of these metals and other metals). A cable may also have within it non-conducting materials and/or coatings, as discussed further below.

A cable is typically dedicated to, and designed for, carrying a single type of electrical signal or therapeutic electricity. For example, a cable may be dedicated to right ventricular (RV) shocking, or to superior vena cava (SVC) shocking, or to sensing cardiac activity. In some cases, a cable may be configured for dual purposes (for example, shocking and sensing), but will typically still be configured to carry only a single electrical signal at a time (for example, either a shocking charge or a sensing signal). Functionally, a cable is equivalent to what may be conventionally viewed as a single conductor or single wire carrying electricity. However, as discussed immediately below, a cable may actually be comprised of multiple filaments of electrically conductive material. At the proximal end, the cable may include means for connection with the ICTD or other therapeutic device, and at the distal end may be an electrode or other element for delivery of therapeutic treatment or for sensing purposes. Other elements may be attached between the proximal and distal ends, connected to the cable via holes in the lumen.

It is noted here that the design of an improved cable for ICTD leads is an advantage of the present cable and lead designs. A cable may be a single conductive element (conventionally referred to as a "solid wire"). However, a cable may also be made of multiple conducting elements as defined briefly here, and discussed further in greater detail, below. These elements may include a central core, and layers which are further comprised of filaments.

Exemplary cables and their elements are illustrated in FIGS. 5-10, discussed further below.

Central Core: A central core is a continuous conducting element of a cable which runs substantially down the geometric center of the cable. In one embodiment of the present cable and lead designs, the central core may be a single filament (defined below). In an alternative embodiment, the central core may be comprised of multiple filaments.

Cable-layer: A cable-layer is a conducting element of a cable which is exterior to the central core. A cable-layer may be wound around the central core. A cable-layer may be composed of one or more conducting filaments (defined below) which may be wound together in parallel, braided together, or otherwise be mechanically coupled to or immediately adjacent to each other. In an embodiment of the present cable and lead designs, and as discussed further below, there may be several filaments in a cable-layer. In an alternative embodiment, a cable-layer may have only a single filament.

Filament (or synonymously in this document, a Wire): A filament or wire is a single, mechanically unitary thread of conducting material. While mechanically unitary, a filament may be composed of multiple materials, possibly in separate layers which are bonded to each other. For example, a filament may have an inner core of a first metal or metal alloy and an outer tube of a second metal or metal alloy, with the layers bonded to each other. Additional layers, and other composite arrangements of bonded, electrically conductive materials, may be possible as well. A filament typically maintains a substantially consistent cross-sectional shape and size for its entire length. The cross-sectional shape may be substantially round or substantially oval, or may be other shapes, as discussed further below. The cross-sectional size may vary depending on the application or placement in the cable. A filament is also sometimes known in the art as a "filar."

Strand: A strand is an element of a cable in which multiple filaments are wound together, typically in a helical or spiral fashion. A strand may have multiple strand layers. Multiple strands may be wound together or otherwise conjoined to form a cable.

In embodiments of the present cable and lead designs illustrated below as exemplary cables 600, 700, 800, and 900 (see FIGS. 6-9), these exemplary cables have only a single strand (with multiple cable-layers, each layer having multiple filaments). In these single-strand embodiments, the "cable" and the "strand" are essentially one in the same, and only the term "cable" is employed.

However, and as illustrated with exemplary rope cable 1100 (see FIG. 11), a cable may have multiple strands. As discussed in further detail below, the elements of the present cable and lead designs may be advantageously employed both in cables with a single strand, and in cables with multiple strands.

A common notation used to describe cables employs the measurements "S×F", where "S" is the number of strands and "F" is the number of filaments. For example, a "1×19" cable has 1 strand with 19 filaments (possibly in two or more cable-layers). A "7×7" cable has 7 strands with 7 filaments per strand.

Jacket (or synonymously in this document, a Coating, Insulation): A jacket or coating is typically a non-conducting material which may be placed around or in contact with a filament, a cable-layer, or the central core.

Dual Cable: The delivery of some therapeutic treatments, or the sensing of some signals, may require more than one cable. For example, two cables may be required to deliver cardiac shocking therapy. Two cables may be placed in parallel within an insulating material, and the two cables may be placed within a single canal within the lumen of the cardiac lead. The dual cables may or may not be separated by their own insulating material.

Coil: A coil is another type of electrically conducting element, typically running the full length or substantially the full length of an ICTD lead. An example is a pacing coil. In a coil, the conducting material is actually coiled or tightly wound, providing additional stiffness. Unless specifically noted otherwise, the conductor cables for small caliber ICTD leads described in detail below are not coils.

Conducting Material: As noted above, a conducting material is any electrically conducting material, including for example and without limitation silver, copper, nickel, chromium, aluminum, iron, molybdenum, tin, platinum, gold, cobalt, tungsten, etc., and/or various alloys of these metals and other metals. Conducting materials may not be limited exclusively to metals, however. For example, a metal alloy with some non-metallic elements (e.g., carbon) may also be an electrically conducting material.

Implantable Leads

The present cable and lead designs are directed towards cable conductors for use in implantable medical leads, such as medical leads used in ICTD device implantation as discussed above with reference to FIG. 1. Exemplary leads 104, 106, 108, 110 may be structurally the same as or similar to exemplary leads 400, 420 discussed in this section with respect to FIGS. 4. Exemplary leads 104, 106, 108, 100 may advantageously employ combinations of elements presented in conjunction with exemplary leads 400, 420 discussed in this section with respect to FIGS. 4. Similarly, exemplary leads 400, 420, as well as leads which may be structurally the same as, similar to, and/or advantageously employ combinations of elements discussed with respect to exemplary leads 400, 420, may be employed in a variety of implantable biomedical applications and other applications as well.

FIG. 4A illustrates an exemplary implantable ICTD lead 400 according to an embodiment of the present cable and lead designs. Lead 400 may for example be suitable for use as any of leads 104, 106, 108, or 110 already discussed above in conjunction with FIG. 1.

Lead 400 has a sheath 405, and five lumens 410a, 410b, 410c, 410d, and 410e. Lumen 410a is a dual lumen configured to contain shocking cables for superior vena cava (SVC) shocking. Lumen 410b is a lumen configured to contain a stylet. Lumen 410c is a dual lumen configured to contain dual cables for right ventricular (RV) shocking. Lumen 410d is configured to contain a single sensing cable to sense cardiac activity. Lumen 410e is configured to contain a pacing coil. Exemplary cables and their elements are discussed further below with respect to FIGS. 5-10.

In one embodiment of the present cable and lead designs there is no liner in the cable lumens. In an alternative embodiment a liner is used in the cable lumens. In an embodiment of the present cable and lead designs the sheath is made from ethylene-tetrafluoroethylene (ETFE).

Persons skilled in the relevant arts will appreciate that lead 400 is exemplary only. The number of lumens shown, the construction of the lumens, the choice of lumens for single cables or double cables, the spacing between the lumens, the application of the lumens for sensing, pacing, shocking, or for a stylet or other stearable elements, are all exemplary. Fewer or more lumens and different configurations of lumens within the lead may be employed within the spirit and scope of the present cable and lead designs.

FIGS. 4B, 4C, and 4D present additional cross-sectional views of the exemplary lead 400 shown in FIG. 4A. The views in FIGS. 4B, 4C, and 4D shows exemplary measurements of elements of lead 400. In FIGS. 4B, 4C, 4D, and also FIG. 4F discussed below, distance measurements are in units of inches, angles are in degrees, R=radius, Ø=diameter. Persons skilled in the relevant arts will appreciate that the measurements shown are exemplary only. Leads with other measurements of elements, such as measurements of the sheath, or measurements of the size and spacing of the lumens, may be employed within the scope and spirit of the present cable and lead designs.

Existing cables for cardiac sensing and/or shocking have, for example, exterior diameters of 0.009" or 0.008", and would not fit within the lumens of lead 400. Exemplary lead 400 is configured for use with the exemplary reduced diameter conducting cables 600, 700, 800, 900, as well as other cables falling within the scope and spirit of the present cable and lead designs, as discussed in further detail below. Such cables have, for example, an outer diameter of 0.007" (i.e., 7 mils).

FIG. 4E illustrates in cross-section another exemplary implantable ICTD lead 420 according to an embodiment of the present cable and lead designs. Exemplary lead 420 is configured for use with the exemplary reduced diameter conducting cables 600, 700, 800, 900, as well as other cables falling within the scope and spirit of the present cable and lead designs, as discussed in further detail below.

Lead 420 has four lumens: lumen 410A configured for SVC shocking; lumen 410B configured for a pacing coil with stylet; lumen 410C for RV shocking; and lumen 410D configured for a sensing cable. Lumen 410A and lumen 410B are designed to hold single cables. In addition all four lumens 410 have liners 415. Notable in FIG. 4E is that lumens 410a and 410c configured to receive cables for cardiac shocking are configured to receive only a single cable. The improved cable conductor designs are configured so that shocking currents may be carried over a single cable, rather than two cables as is required in existing designs.

FIG. 4F is another cross-sectional view of the exemplary lead 420 shown in FIG. 4E. FIG. 4F displays exemplary measurements of the various elements such as sheath 405, lumens 410, and liners 415.

Persons skilled in the relevant arts will appreciate that the views of exemplary leads shown in FIGS. 4A-4F represent cross-sectional views only. Orthogonal to the cross-sectional views shown are the lengths of the leads, which are elongated flexible tubular elements, wherein the lumens are configured to receive such elements as cables, coils, or stylets. Cables and coils are used for such purposes as conducting electrical signals or electrical impulses for cardiac sensing and cardiac shocking.

Cables Used in Leads, Fretting Fatigue and Failure Modes in the Cables

FIG. 5A illustrates an exemplary cable 500. Exemplary cable 500 has a central wire (or core) 505 which, in an embodiment, is a single wire or filament of a conducting material, such as a metal or a metal alloy. In an alternative embodiment, the central core may actually be comprised of multiple filaments which are wound together or otherwise mechanically coupled (not shown in FIG. 5A).

Surrounding central wire 505 is a cable-layer such as cable-layer 510.i which is an inner cable-layer, and which is composed of multiple filaments 515. The filaments 515 of cable-layer 510.i are wound around central core 505 in a helical fashion.

Surrounding inner cable-layer 510.i is a second cable-layer, namely a middle cable-layer 510.m, which is also composed of multiple filaments 515. Filaments 515 of cable-layer 510.m are wound around cable-layer 510.i, again in a helical fashion. Surrounding middle cable-layer 510.m is outer cable-layer 510.o which again is composed of multiple filaments 515, this time wound helically around middle cable-layer 510.m.

It will be noted in FIG. 5A that filaments 515 have a substantially circular cross-section as is commonly found in the art. Likewise, central core 505 has a substantially circular cross-section.

Cable-layers 510, and more specifically the filaments 515 of a cable-layer 510, may be wound with a helical or spiral winding around the element inner to them, such as an inner cable-layer 510.i or central wire 505. Persons skilled in the relevant arts will appreciate that the configuration of central wire 515, inner cable-layer 510.i, middle cable-layer 510.m, and outer cable-layer 510.o shown in FIG. 5A is exemplary only. Fewer cable-layers, more cable-layers, fewer filaments, or more filaments may be employed.

Figure 5C:
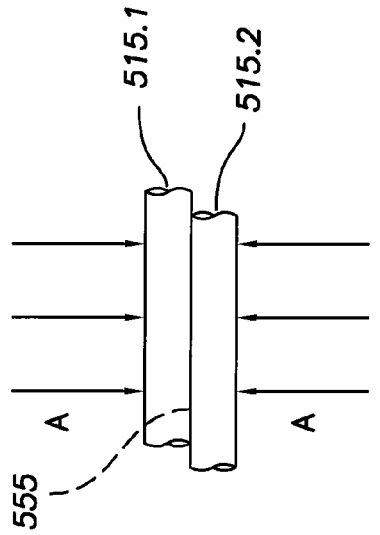
FIG. 5C illustrates a contact mode between two adjacent filaments which are part of a single cable-layer of a cable.
Figure 5D:
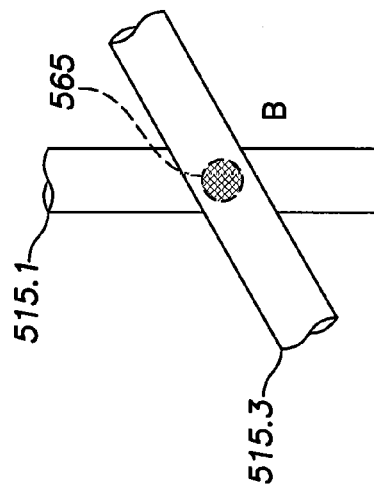
FIG. 5D illustrates a contact mode between two filaments, each filament being part of a respective one of two adjacent cable-layers of a cable.
Figure 5B:
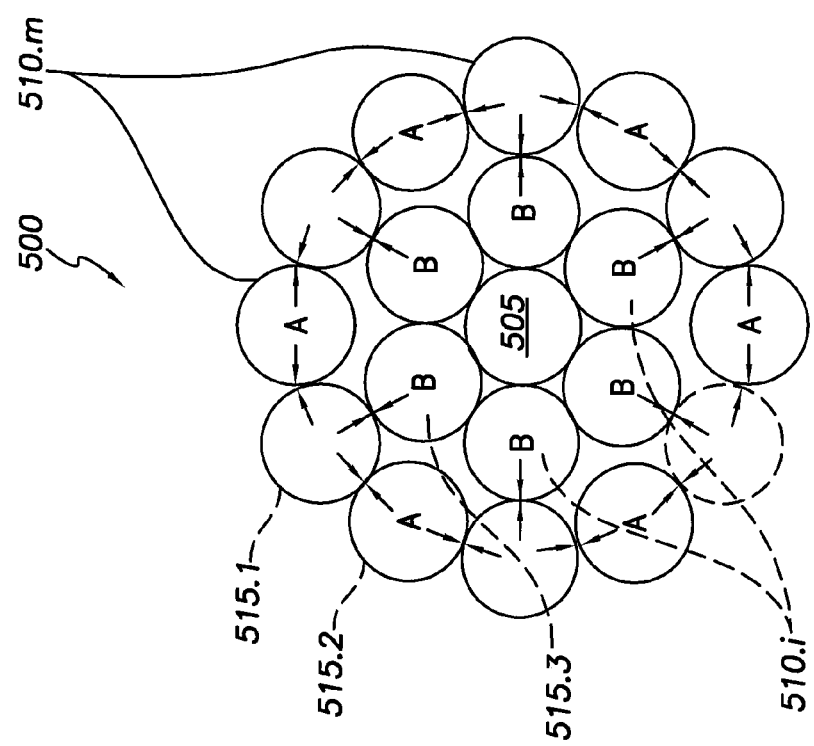
FIG. 5B illustrates a cross-sectional view of the cable shown in FIG. 5A.

FIG. 5B is a partial cross-sectional view of the cable 500 shown in FIG. 5A. The cross-sectional view shows middle cable-layer 510.*m*, inner cable-layer 510.*i*, and central wire 505. (Outer cable-layer 510.*o* is omitted.) Also shown are points of contact, and therefore points of pressure, between filaments 515 of the cable-layers. For example points of contact 'A' exist between filament 515.1 and 515.2 of middle cable-layer 510.*m*. Points of contact 'B' also exist between filament 515.3 of inner cable-layer 510.*i* and filament 515.1 of middle cable-layer 510.*m*. Not shown, but present in cable 500, is contact and pressure between filaments 515 of inner cable-layer 510.*i* and central wire 505.

Because filaments 515 in a common cable-layer 510 typically are configured to run in parallel to each other, there is a substantially continuous line of contact between adjacent filaments. FIG. 5C illustrates a line of contact 555 between two filaments 515.1 and 515.2 of middle cable-layer 510.*m* (see FIG. 5B). The direction of force or pressure between filaments 515.1, 515.2 is indicated by arrows A, consistent with pressure indicated by arrows A in FIG. 5B. While contact between filaments 515.1 and 515.2 is illustrated as line 555, persons skilled in the relevant arts will appreciate that compression between filaments 515.1 and 515.2 actually results in a narrow, elongated area of contact 555, which for convenience is referred to a "line of contact."

In cable-layers 510 which are adjacent to each other or between an inner cable-layer 510.*i* and the central core 505, filaments 515 are not wound in identically parallel helices. (See again FIG. 5A, where filaments 515 of cable-layer 510.*o* are not wound in parallel to filaments 515 of adjacent cable-layer 510.*m*, and filaments 515 of cable-layer 510.*m* are not wound in parallel to cable-layers 515 of adjacent cable-layer 510.*i*.) As a result, contact between filaments 515 in adjacent cable-layers 510 is made along a small contact area which may be referred to as a point of contact. Also, contact between filaments of an inner cable-layer 510.*i* and a central core 505 may again be made along a small contact area which may be referred to as a point of contact.

FIG. 5D illustrates a contact mode between two filaments 515 of two adjacent cable-layers, which may for example be filament 515.1 of middle cable-layer 510.*m* and filament 515.3 of inner cable-layer 510.*i* (see FIG. 5B, discussed above). The small area of contact 565 may be referred to as point of contact 565, and is located between the two filaments 515.1, 515.3. (It is illustrated in FIG. 5D with a dashed line and a shaded interior to indicate it is actually between the filaments, and not on a surface of filament 515.3 opposite to filament 515.1.) The direction of force or pressure 'B' at point of contact 565 is into the page from the filament 515.3 illustrated as the top filament, and out of the page from the filament 515.1 illustrated as the bottom filament, and is consistent with pressure indicated by arrows B in FIG. 5B.

The reference to filaments as "top" and "bottom" is made with reference to the illustration only, is for convenience of explanation, and is not intended to be limiting. Contact between filaments 515 may occur between filaments within any cable-layer 510, between filaments 515 of any two adjacent cable-layers 510, and between filaments 515 of a cable-layer 510 and central wire 505.

The contact point 565 between filaments 515.1 and 515.3 of adjacent cable-layers 510.*m* and 510.*i* is referred to as the point of Trellis contact between filaments 515.1 and 515.3. The overall configuration of filaments 515 in adjacent cable-layers 510 pressing against each other at Trellis contact point 565 is referred to as Trellis contact mode. Both line contact mode and Trellis contact mode at respective contact lines/points 555 or 565 between cable-layers 515 are locations where fretting fatigue may occur.

Fretting fatigue is a wear phenomenon occurring between two surfaces having oscillatory relative motion of small amplitude. Fretting is generally associated with contact surfaces which are held together in some manner, often by a mechanical connection (such as clamping, or elements which are twisted or crimped together) and where the surfaces in contact are nominally at rest. Put another way, while there is relative motion between the elements making contact, the body which contains them as a whole may be in a substantially static, global equilibrium. At the same time, the elements in contact experience some small-scale, relative oscillatory or vibratory motion.

These conditions occur between the filaments of a cable inside an ICTD lead 400, 420. While lead 400, 420 as a whole may be substantially at rest (relative to a patient's body, or relative to a patient's heart), small but continual sources of movement (such as movement of cardiac muscles, circulation of blood surrounding the lead, etc.) cause small movements of lead 400, 420. This in turn causes filaments 515 within lead cables 500 to experience small relative motion, and this results in fretting fatigue along line of contact 555 and Trellis contact point 565.

Fretting contact causes detrimental effects since it leads to wear. In addition, tensile stresses from the contact promote crack initiation and propagation. These fatigue cracks can lead to component failure, such as a breaking of filaments 515. Trellis contact mode dominates the fretting fatigue, the key failure mode of a cable, due to the smaller contact area of Trellis contact point 565 relative to line of contact 555, and also due to larger frictional sliding motions that generate larger alternating stresses or strains on the filaments 515 between adjacent cable-layers 510.

Further, fretting fatigue at either line of contact 555 or Trellis contact point 565 is more likely to cause filament failure than stresses internal to filaments 515, since the filament surfaces are where manufacturing defects are most likely to exist.

Figure 5E:
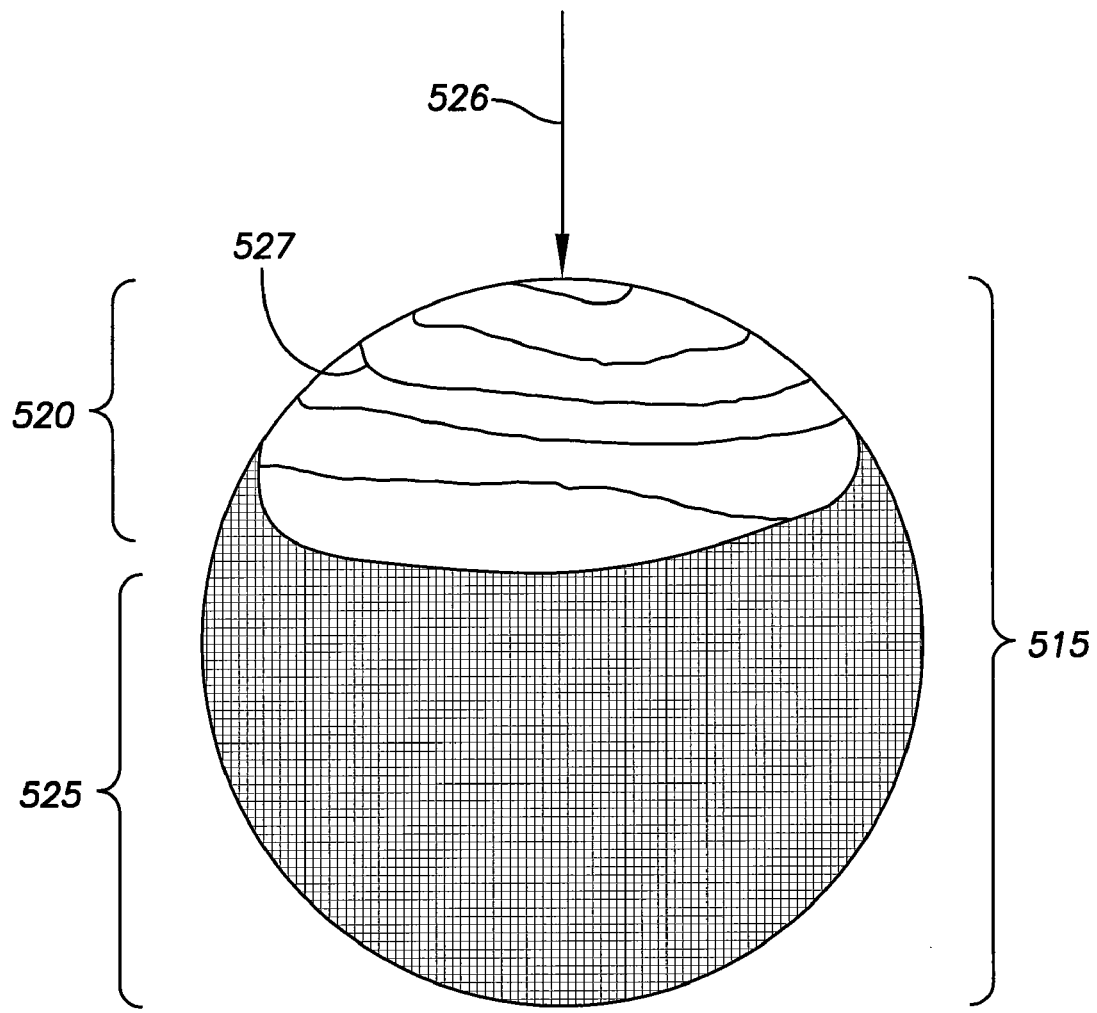
FIG. 5E illustrates a fretting fatigue fracture morphology of a fine wire filament of a cable subjected to cyclic flex loading.

FIG. 5E illustrates a typical fretting fatigue fracture morphology of a fine wire filament of a cable subjected to cyclic flex loading. The view shown is a cross-sectional view of a filament 515. Filament 515 has a fatigue life which may be measured in terms of stress cycles, representing a number of vibrations or cyclic stress pressures that filament 515 can experience before undergoing physical fracture. For example, the fatigue life may be on the order of 100,000,000 cycles.

If filament 515 consistently experiences pressure, stresses, and/or vibrations at a consistent point and in a consistent direction, as represented for example by pressure arrow 526, then filament 515 will have a fatigue zone 520 extended from the point of contact of pressure arrow 526 inward towards the interior of filament 515. Approximately 90% to 99% of the fatigue life of filament 515 is absorbed in fatigue zone 520. When pressure 526 exceeds a fatigue threshold (which may vary depending on the materials and configuration of filament 516), fatigue zone 520 experiences progressive inward degradation, represented by fatigue lines 527. That is, damage to filament 515 propagates inward over time, with repeated stresses and vibrations on the surface of filament 515.

Fast fracture zone 525 takes approximately 10% or less of the total fatigue life. However, when the fatigue caused by pressure or force 526 reaches fast fracture zone 525, filament 515 has a high likelihood of experiencing fracture, that is, a complete break of the filament.

It is an advantage of the present cable and lead designs to modify both the structure of filament 515 and the interaction of filament 515 with the surrounding environment, such that pressure 526 on filament is less likely to reach the fatigue threshold. If the fatigue threshold is not reached, cycles of the fatigue life are not used up, and filament 515 is much less likely to experience fracture, or at least is likely to have a greatly prolonged life before fracture. The various elements disclosed in detail below may reduce the pressure experienced by filament 515 by anywhere from 30% to 90% lower as compared with existing designs.

Cable Designs for Reduced Diameter with Optimized Mechanical and Electrical Properties—Overview The structural features of the conductor cables of the present cable and lead designs are discussed in detail below in a later section with respect to FIGS. 6-10, and corresponding exemplary cables 600, 700, 800, and 900 (discussed in respective FIGS. 6, 7, 8, and 9, as well is in FIG. 10). In some of the discussion below, and for convenience of reference only, these exemplary cables 600, 700, 800, 900 are referred to collectively herein as cables 600/900. It will be understood that not all the features listed here will necessarily be employed in each of exemplary cables 600/900, and further that other embodiments of the present cable and lead designs, apart from exemplary cables 600/900, and employing some or all of the elements listed in this section, will fall within the scope of the present cable and lead designs. Thus, references below to "exemplary cables 600/900" should be understood to include not only exemplary cables 600, 700, 800, and 900, but all embodiments which may employ, in various combinations, the elements and advantages described herein.

Similarly, exemplary filaments 615, 715, 815, and 915 which may have oval cross-sections and/or other distinguishing features are described in detail below with reference to FIGS. 6-10. These exemplary embodiments, as well as other filaments with oval cross-sections or other distinguishing features falling within the scope of the present cable and lead designs, are referred to collectively herein for brevity as filaments 615/915. Here again it will be understood that not all the features listed here will necessarily be employed in each of exemplary filaments 615/915, and further that other embodiments of the present cable and lead designs, apart from exemplary filaments 615/915, and employing the features and advantages discussed below, will fall within the scope of the present cable and lead designs. Thus, references to "exemplary filaments 615/915" should be understood to include not only exemplary filaments 615, 715, 815, and 915, but all embodiments which may employ, in various combinations, the features described herein.

Similarly, exemplary cable-layers with filaments 615/915 and/or other distinguishing features 610, 710, 810, and 910 are described in detail below with reference to FIGS. 6-9. These exemplary embodiments, as well as other cable-layers falling within the scope of the present cable and lead designs, are referred to herein for brevity as cable-layers 610/910. Here again it will be understood that not all the elements and advantages described herein will necessarily be employed in each of exemplary cable-layers 610/910, and further that other embodiments of the present cable and lead designs, apart from exemplary cable-layers 610/910, and employing the elements and advantages listed herein, will fall within the scope of the present cable and lead designs. Thus, references to "exemplary cable-layers 610/910" should be understood to include not only exemplary cable-layers 610, 710, 810, and 910, but to all embodiments which may employ, in various combinations, the features and advantages described herein.

Additional features described in this section and succeeding sections in general terms may also be represented by exemplary embodiments discussed later in this document. Suitable labels will be presented, and will be understood with references to various figures as indicated.

It will be understood by persons skilled in the relevant arts that cables 600/900 may have some elements in common with cables 500 discussed above, along with various distinguishing elements and advantages. Similarly, it will be understood that filaments 615/915 may have some elements in common with filaments 515 already discussed above, along with various distinguishing features. Similarly, it will be understood that cable-layers 610/910 may have some elements in common with cable-layers 510 already discussed above, along with various distinguishing features.

The features of the conductor cables 600/900 of small caliber ICTD leads 400, 420 of the present cable and lead designs are discussed here. These features make it possible to employ these conductor cables 600/900 with all types of ICD, CRT, and Brady leads 400, 420 for active or passive fixation.

Cable Designs Overview—Mechanical and Structural Elements

The mechanical performance of the conductor cables 600/900 (discussed in specific detail below with respect to FIGS. 6-10) is optimized with respect to currently existing cables to have higher tensile strength (approximately three to six lbs.), less flex/bending stiffness, lower fretting fatigue failure risk, and lower chance of failure due to kinking and bird-caging. This advantageous mechanical performance is achieved via a variety of elements, used alone or in various combinations, including, for example and without limitation:

A. The use of filaments 615/815 with substantially oval cross-sections as the cable filaments. (It is noted here that exemplary filament 915, discussed in connection with exemplary cable 900 of FIG. 9, does not use an oval cross-section, and instead retains a substantially circular cross-section. Hence reference is made here to exemplary filaments 615, 715, and 815, or 615/815, discussed in conjunction with FIGS. 6, 7, 8, and 10.) The oval shape filaments are structurally arranged in a manner which increases the Trellis contact surface areas between cable-layer layers 610/810, which decreases the contact pressure or stress. Therefore, the fretting fatigue failure risk of cables 600/800 is decreased. The stationary oval shape filaments can be wound around a rotating and translating center round wire or around a mandrel for the cables or cable-layers. Filaments with oval cross-sections also offer a larger cross sectional area for a given cable diameter; they therefore have higher tensile strength than the round shape filaments 515 in the traditional cables 500.

In an embodiment of the present cable and lead designs, all the cable-layers employ filaments with substantially oval-cross sections. In an alternative embodiment, some cable-layers employ filaments with substantially oval cross-sections, while some cable-layers employ filaments with substantially circular cross sections or other cross sections.

B. A polymer coating or jacket on the filaments may be placed between cable-layers. This changes the contact interaction mode from hard to soft contact between the filaments, which decreases the contact pressure, and therefore, the fretting fatigue failure risk of the cables.

C. The cross sectional area of the filaments may decrease gradually and progressively from the center wire 605/905, to one or more middle cable-layers 605.$m$/905.$m$, and finally to the outer-most cable-layer 605.$o$/905.$o$. The result is that the cable 600/900 can offer higher tensile strength but less flex stiffness.

In an embodiment of the present cable and lead designs, the cross-sectional area decreases progressively with outward radius from the central wire 605/905, with any cable-layer 610/910 having filaments 615/915 of smaller cross-sectional area than the filaments 615/915 of any cable-layer 610/910 or core 605/905 interior to it.

In an alternative embodiment, some adjacent cable-layers 610/910 may have filaments 615/915 of the substantially same cross-sectional area. In an embodiment, a cable 600/900 may have only a central core 605/905 and single cable-layer 610/910 surrounding the central core 605/905, with the filaments 615/915 of the single cable-layer 610/910 having a smaller cross-sectional area than the filament 615/915 of the single core 605/905.

D. Varying materials or material strengths (e.g., MP35N, DFT with different silver content, etc.) may be used for the filaments 615/915 in different cable-layers 610/910 (i.e., different layers). In an embodiment, the strength of the materials decreases from the center wire 605/905 to one or more middle cable-layers 610/910 to the outer cable-layer 610/910, such that the cable 600/900 will offer higher tensile strength but less flex/bending stiffness. This is discussed in further detail with regard to FIG. 10, below.

E. Proper heat treatment, such as the so-called kill-temperature with the wire/cable cold work process, may be employed to provide desired high ductility and high strength of the wire material, such as MP35N, DFT, etc.. Usually a ductile material offers lower tensile strength; the tensile strength of approximately 4 lb. per cable may be achieved when using the kill-temperature heat treatment for a small size 1×19 cable which employs the DFT filaments with silver wire content up to 50%, since most of the wire strength is from the MP35N tube which surrounds the wire's silver core.

1×19 cables with the mechanical design features described above offer the dimensions of down-sized cables that can meet the requirements for the smaller ICD leads 400, 420 of 5 French or less. These cable designs can be expanded to other cable structures of single strand cables, such as 1×7, 1×25, and multiple strand cables, such as 7×7. Moreover, a single cable designed with one or more of the above features can replace the dual cables used in some ICTD leads 400 without loss of the pull strength, and at the same time offer less flex stiffness.

F. The currently practiced laser welding, crimping, etc. joining technologies for the dual cables in the some ICTD leads can be used for the single cable leads with minor modifications, when the insulation coatings or jackets on the filaments 615/915 or between cable-layers 610/910 are stripped or ablated (such as the soda blast process) at each end of the cable before the joining process. The cable-ring and cable-shock coil joining technology would deliver the same joining quality for either the dual or single cable designs.

Cable Designs Overview—Electrical and MRI Performance

The electrical and MRI performance of the conductor cables 600/900 is optimized with respect to cables 500 to have a lower, stable DC resistance, good electrical conductivity, higher and stable inductance, and only minor electromagnetic interactions between conductor cables 600/900 and coils. This optimized electrical and MRI performance is achieved via a variety of features, used alone or in various combinations, some of which are the same as the mechanical/structural elements already discussed above, and which may include, for example and without limitation:

A. Oval-shaped cross-sectional filaments 615/815, already discussed above, offer a larger cross section area for a given cable 600/800 diameter. This results in cable 600/800 having lower DC resistance than the round-shaped filaments 515 in cables 500.

B. For each cable 600/900 within a lead 400, 420, the polymer (ETFE, PTFE, Polyimide, Paryline, PFA, etc.) coatings or jackets 615, 730, 825, 830, 925, 930 on the cable filaments 615/915, or between cable-layers 610/910 (i.e., between layers, or between the central wire 605/905 and the immediately exterior cable-layer 610/910) will insulate the filaments 615/915 within the lead 400, 420 body (i.e., for the length of the lead body). However, the polymer coatings or jackets will be removed (for example, stripped or ablated) at each end of the filaments 615/915 (i.e., at the proximal and distal ends of leads 400, 420), and for each cable 600/900 the filament 615/915 ends without the insulation materials are joined together (see above Mechanical item F) with the proximal pin and distal electrode, by means of crimping, for example. The result is that the multiple filaments 615/915 within a cable 600/900 will form parallel circuits in the lead body 400, 420. Such an insulated cable circuit is similar to those in the insulated coils which have been proven, experimentally, to offer lower DC resistance and higher inductance.

C. Higher silver content DFT filaments may be designed for the cable filaments 615/915, from the current practice of 28% and 31% increasing up to about 50% (see above tensile strength and fatigue performance descriptions), such that the DC resistance can be reduced to approximately 0.6 ohm per foot for cable 600/900. As a result, the single cable's DC resistance will be substantially equivalent to the dual cables in some designs of existing ICTD leads, which will maintain a large current carrying capability of up to 50 A as required by the international standard (Section 23.3 of the prEN45502-2-2:2006, Active Implantable Medical Devices, published by the CEN/CENELEC Joint Working Group Active Implantable Medical Devices of the European Committee for Electrotechnical Standardization).

D. With the mechanical features discussed above, it is possible to wind the filaments 615/915 in each cable-layer 610/910 of a cable 600/900 with a smaller pitch (that is, a steeper degree of inclination or slope) compared to conventional cable designs 500. The smaller pitch can be achieved without concerns of increasing the flex stiffness or concerns of higher contact stresses generated in the filaments 615/915 between layers, since the specific cable structure design features discussed herein compensate for the smaller pitch. The smaller pitch results in more turns of the cable winding (i.e., more turns of filaments 615/915) for a given lead body length, and so offers a larger inductance. This benefits the low-pass filter function of cable 600/900, and enhances the MRI radio-frequency (RF) heating reduction, as observed in the MRI scans of coils wound with different pitch lengths.

E. Many existing lead designs require dual cables for such purposes as cardiac shocking. The dual cables in a single lumen are problematic for patients who must undergo MRI tests. The distance between the two conductor cables in a lumen may change any where in the lead body (as the lead is moving or deforming), and consequently the parasitic capacitance along the cables will vary in a large range in a manner difficult to control. This can result in undesirable heating of the cable during an MRI.

The present design enables the substitution of a single cable 600/900 where two cables were previously employed in a single lumen. The single cable can avoid the unstable or non-consistent electromagnetic interactions between the two cables inside the same lumen. This is beneficial for the MRI RF heating reduction.

Cable Designs Exemplary Embodiments

In FIGS. 6-10, where exemplary cables 600/900 are illustrated in embodiments of the present cable and lead designs, only two cable-layers 610/910 are illustrated exterior to the central wire 605/905. These are referred to as, for example, a "middle cable-layer 610.*m*" and an "outer cable-layer 610.*o*." This is for convenience in labeling only. In these contexts, "middle cable-layer 610.*m*" could as easily be referred to as "inner cable-layer 610.*i*." However, the term "middle cable-layer 610.*m*" is preferred in the sense that, in alternative embodiments, additional middle cable-layers 610.*m* could be employed (for example, a second middle cable-layer, and/or a third middle cable-layer, etc,), and much of the discussion which pertains to the middle cable-layers illustrated in FIGS. 6-10 could apply to additional middle cable-layers as well.

Figure 6A:
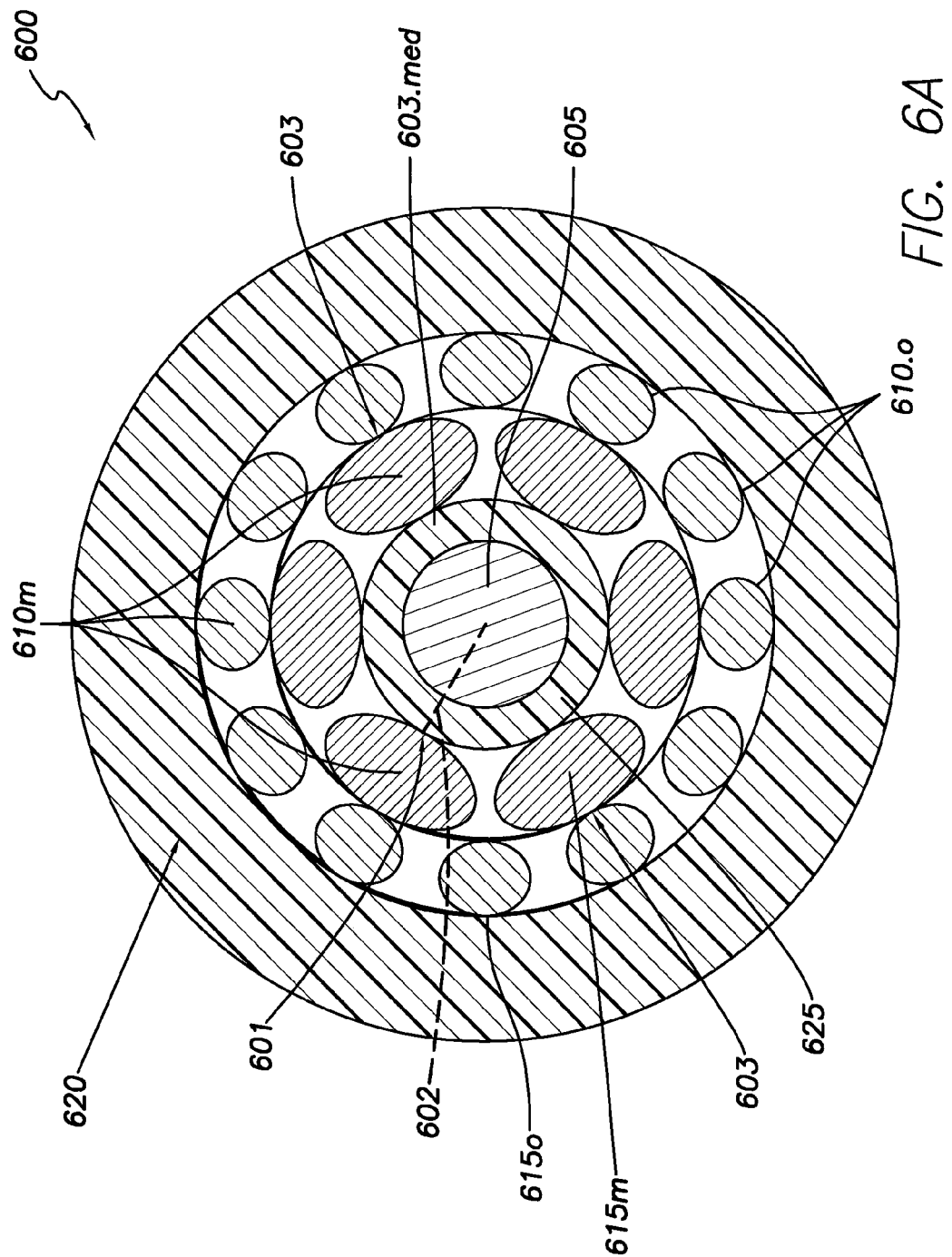
FIG. 6A illustrates an exemplary cable configured for improved mechanical and electrical properties according the present cable and lead designs.

FIG. 6A illustrates an exemplary cable 600 configured for improved mechanical and electrical properties. Cable 600 has a central wire 605, a middle cable-layer 610.*m*, an outer cable-layer 610.*o*, a central wire coating 625, and a cable jacket 620.

Several features of exemplary cable 600 can be immediately observed from FIG. 6A. A first feature is that the filaments 615 of cable-layers 610 have a substantially oval cross-sectional shape. That is, exemplary filament 615.m of middle cable-layer 610.*m* has a substantially oval shape, and exemplary filament 615.*o* of outer cable-layer 610.*o* also has a substantially oval cross-sectional shape. Persons skilled in the relevant arts will appreciate that while the shape illustrated is substantially oval, it is not necessary that the shape of a filament 610 be perfectly ovoid. Filament 615 has two orthogonal axes, both perpendicular to the length of filament 615 (which extends into and out of the page), a first axis of which is substantially longer than a second axis, resulting in a substantially flattened shape of the filament 615 as compared with a circular shape of filament 515 (see FIG. 5).

It is further to be noted from the figure that the elongated surfaces of filaments 615 in adjacent cable-layers 610 are substantially in contact with one another and substantially parallel to one another. That is, for example, a first flat surface (not shown) which could be placed tangent to an elongated surface of filament 615.*m* of middle cable-layer 610.*m* is substantially parallel to a second flat surface (not shown) which could be placed tangent to an elongated surface of filament 615.*o* of outer cable-layer 610.*o*. Another way to understand the orientation of oval-cross section filaments 615 is to visualize a line 602 extending from the mid-point 601 of an elongated surface of a filament 615, and drawn normal to the elongated surface in the plane of the cross-section. Line 602 will extend towards a point which is in substantial proximity to the geometric center of the cross-sectional area of cable 600. (It should be noted that line 602 is shown for visualization only, and not a structural element of cable 600.)

At locations 603 of parallelism between elongated surfaces of filaments 615.*o* and 615.*m*, the surfaces of filaments 615.*o* and 615.*m* are in contact. As a result of the contact between these elongated surfaces, the pressure between filaments 615 in adjacent cable-layers 610 is distributed over a wider contact surface area. As a consequence of distributing the pressure between the filaments over a wider contact surface area, the pressure per unit area is reduced on each filament 615. This reduced pressure per unit area results in decreased fretting fatigue, decreased structural damage to each filament 615, and therefore increased durability and lifetime for cable 600 as a whole.

It can be seen from the figure that similar elongated but mediated contact areas 603.med will exist between filaments 615.*m* of middle cable-layer 610.*m* and central wire 605. In this case, as well as in the case of other embodiments of cables discussed below (in conjunction with FIGS. 7-10), the contact region between filament 615 and central wire 605 is a mediated contact region 603.med which is mediated by a non-conducting coating 615 or other coatings. (See also coatings 730, 825, 830 discussed below in conjunction with FIGS. 7-8.)

However, even with coating 615 or other coatings, the region or area of mediated contact pressure 603.med is still enlarged relative to that for filaments 515 with strictly circular cross sections (see for example FIG. 5 above). As a result, surface pressure per unit area on filaments 615 or central wire 605 is reduced, and again the reduced pressure per unit area results in decreased fretting fatigue, decreased structural damage to each filament 615, and therefore increased durability and lifetime for cable 600 as a whole Other advantages of the substantially oval shape of the filaments have already been discussed above, and that discussion will not be repeated here. A further feature of cross-sectional view of exemplary cable 600 is that the cross-sectional area of a filament 615 decreases progressively along an axial radius from the central core. That is that central core or central wire 605 has the largest cross-sectional area. Filaments 605.*m* of middle cable-layer 610.*m* have a lesser cross-sectional area than central wire 605. And similarly filaments 605.*o* of outer cable-layer 610.*o* have a substantially smaller cross-sectional area than filaments 615.*m* of middle cable-layer 610.*m*. The advantages of reducing the cross-sectional area have already been discussed above and the discussion will not be repeated here.

A further feature of exemplary cable 600 not visible in the figure is that the metallic structure of the filaments 615 may change in going from central wire 605 to middle cable-layer 610.*m* to outer cable-layer 615.*o*. A detailed discussion of this change in metallic structure of filaments 615 is provided below, in conjunction with FIG. 10.

An additional feature of exemplary cable 600 is central wire coating 625. Central wire coating 625 may be comprised of a variety of polymers such as, for example and without limitation, silicone rubber, polyurethane, Optim, PTFE, polyimide, paryline, PFA, etc. Central wire coating 625 further serves to reduce fretting fatigue between middle cable-layer 610.*m* and central wire 605.

Persons skilled in the relevant arts will appreciate that the exact configuration shown for cable 600 is exemplary only, and in implementation may vary in any number of details. For example, shown in FIG. 6A is central core 605, middle cable-layer 610.*m*, and outer cable-layer 615.*o*. More cable-layers or fewer cable-layers may be employed. Similarly, the number of filaments 615 used in each cable-layer is exemplary and may be vary in actual implementation. Similarly, the relative sizes of the filaments 615 are exemplary only and may vary in actual implementation. Similarly, the relative size of cable jacket 620 and central wire coating 625, relative to other elements is exemplary only and may vary in actual implementation.

Figure 6B:
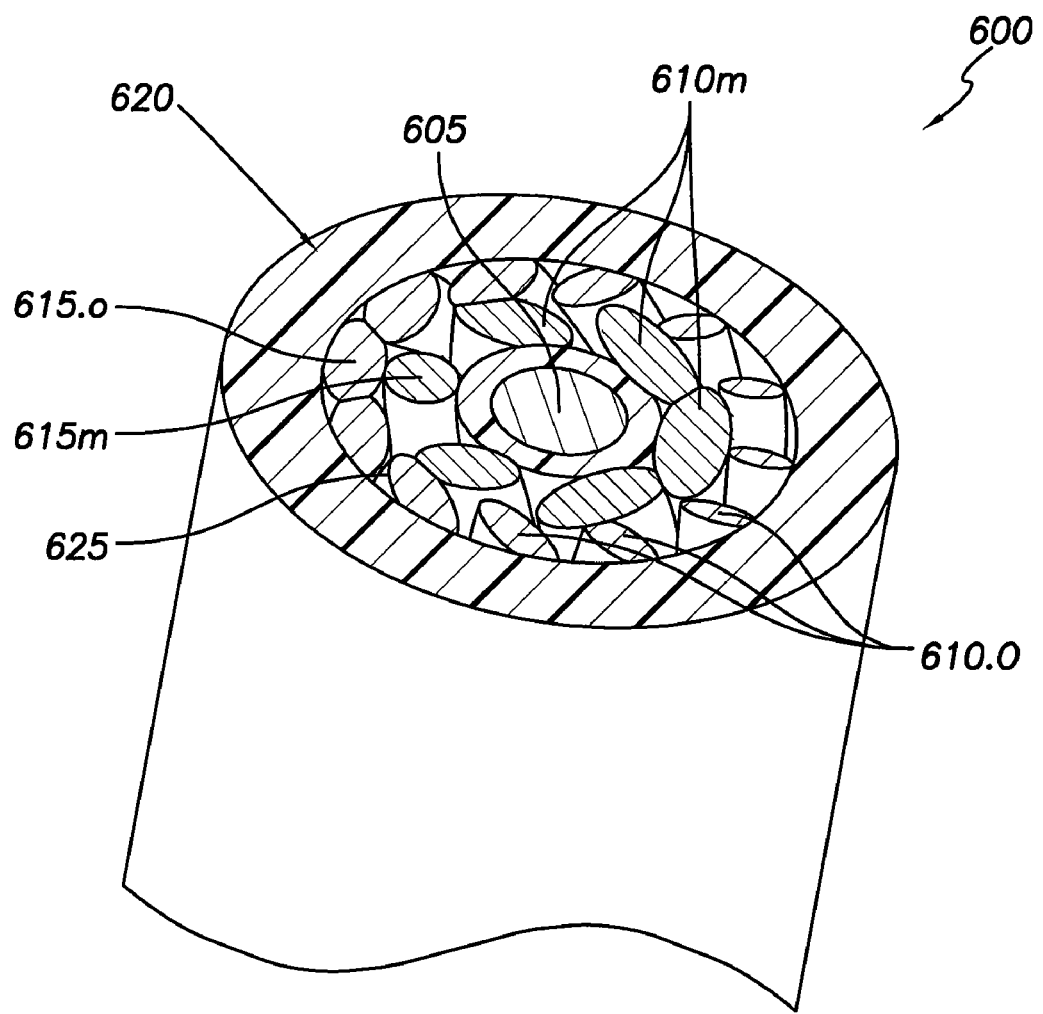
FIG. 6B illustrates another view of the exemplary cable shown in FIG. 6A.

FIG. 6B is another view of exemplary cable 600. This view illustrates the extended length of the cable and in addition illustrates the helical winding of filaments 615.*o* and 615.*m*.

Figure 6C:
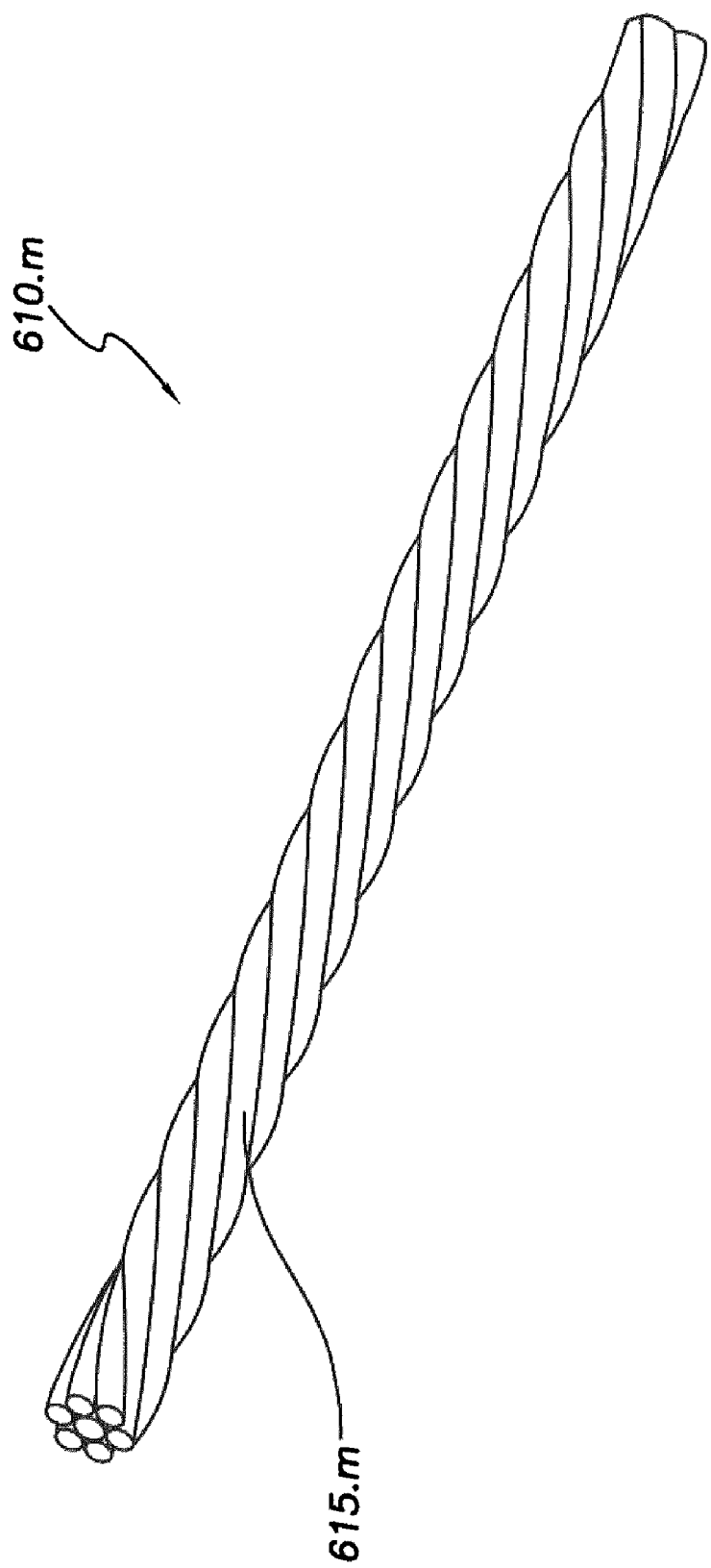
FIG. 6C illustrates an exemplary cable-layer of the cable shown in FIG. 6A.
Figure 6D:
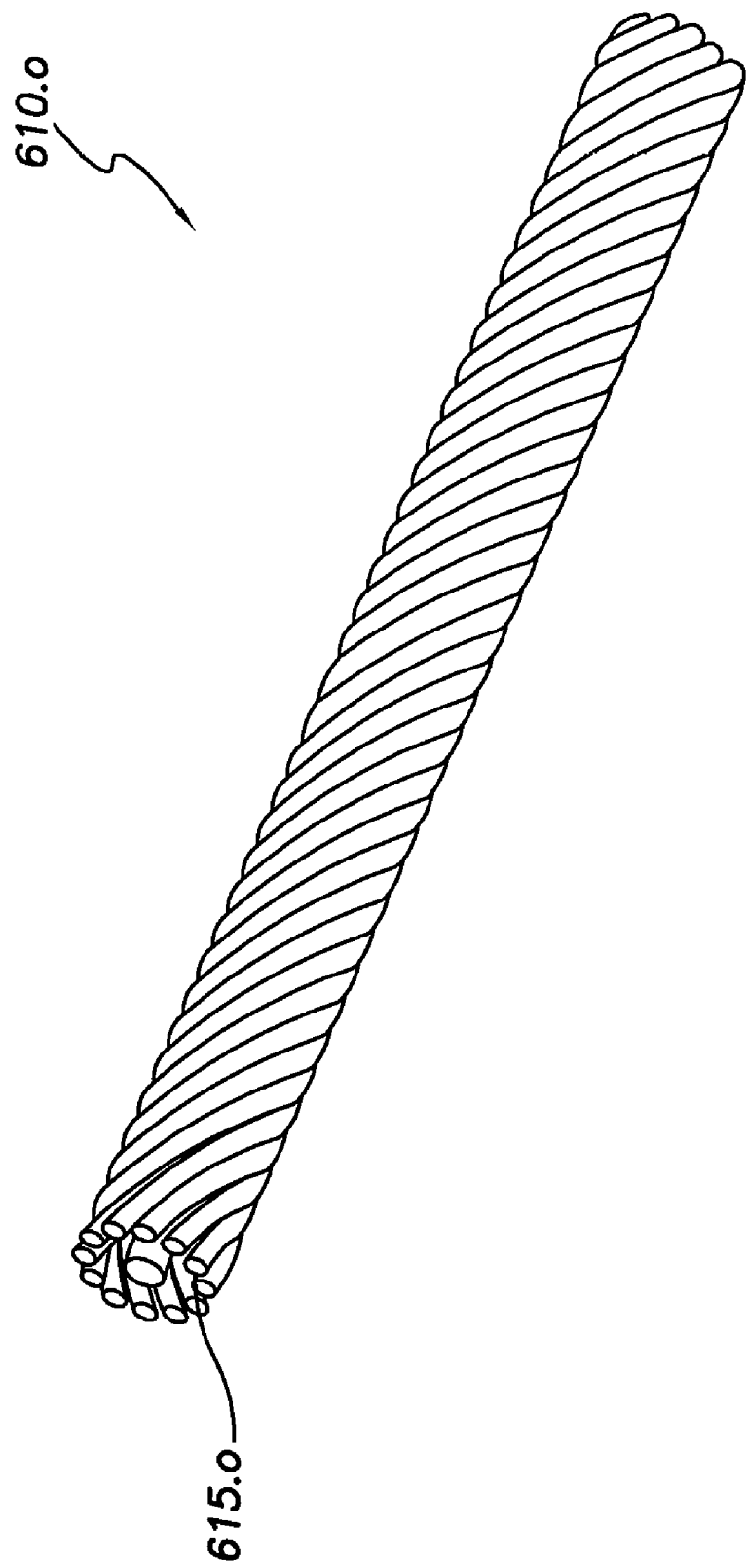
FIG. 6D illustrates another exemplary cable-layer of the cable shown in FIG. 6A.

Also shown in FIG. 6B is that central wire 605 has a 28% silver content. In FIGS. 6C and 6D (discussed further below) it is shown respectively that mid-layer cable-layer 610.*m* features filaments 615.*m* with 33% silver content and outer cable-layer 610.*o* features filaments 615.*o* with 41% silver content. The amount of silver content is exemplary only, and may vary in different embodiments. Further details of the filament metallic structure and content are presented below with respect to FIG. 10.

It is illustrated in FIG. 6B that alternate cable-layers 610 may be wound in alternate directions. For example, middle cable-layer 610.m may be left hand wound while outer cable-layer 610.o may be right hand wound. As shown in FIGS. 6C and 6D respectively, the pitch of the winding may vary as well. For example, middle cable-layer 610.m may have a left hand winding with a pitch of 0.045 inches, while outer cable-layer 610.o may have a right hand winding with a pitch of 0.036 inches. It is again noted that the windings and pitches employed are exemplary only. Persons skilled in the relevant arts will appreciate that other windings and other pitches are possible within the scope and spirit of the present cable and lead designs. In general, the smaller the cross-sectional area of the filaments 615 in a cable-layer 610, the tighter the windings may be.

Figure 6E:
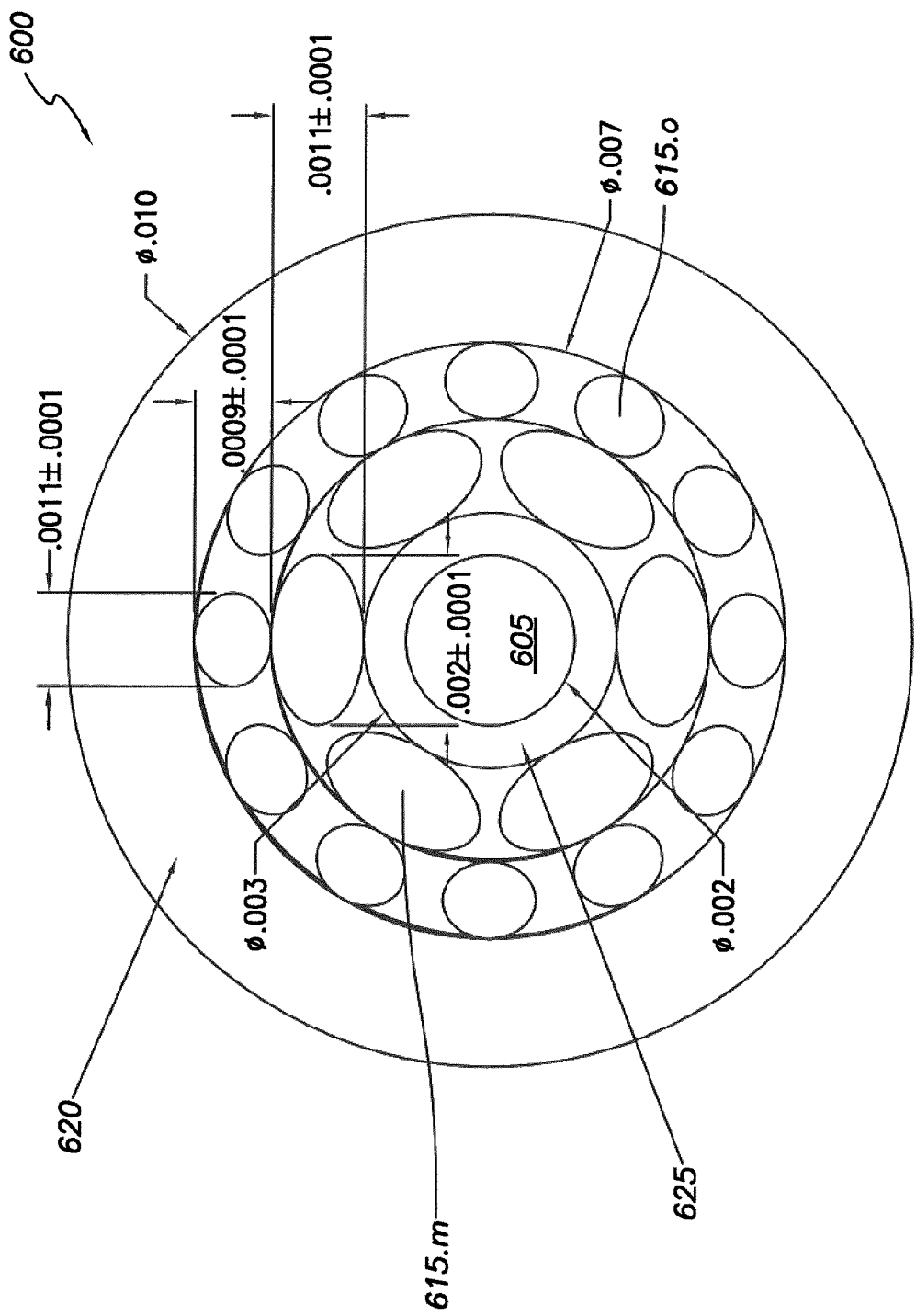
FIG. 6E illustrates another view of the exemplary cable of FIG. 6A.

FIG. 6E is another cross-sectional view of exemplary cable 600 configured for improved mechanical and electrical properties. FIG. 6E includes features already discussed in detailed above and the discussion will not be repeated here. Also, included in FIG. 6E are exemplary measurements of various elements of exemplary cable 600. It will be appreciated that these measurements are exemplary only and other measurements may be employed within the scope and spirit of the present cable and lead designs.

Figure 7A:
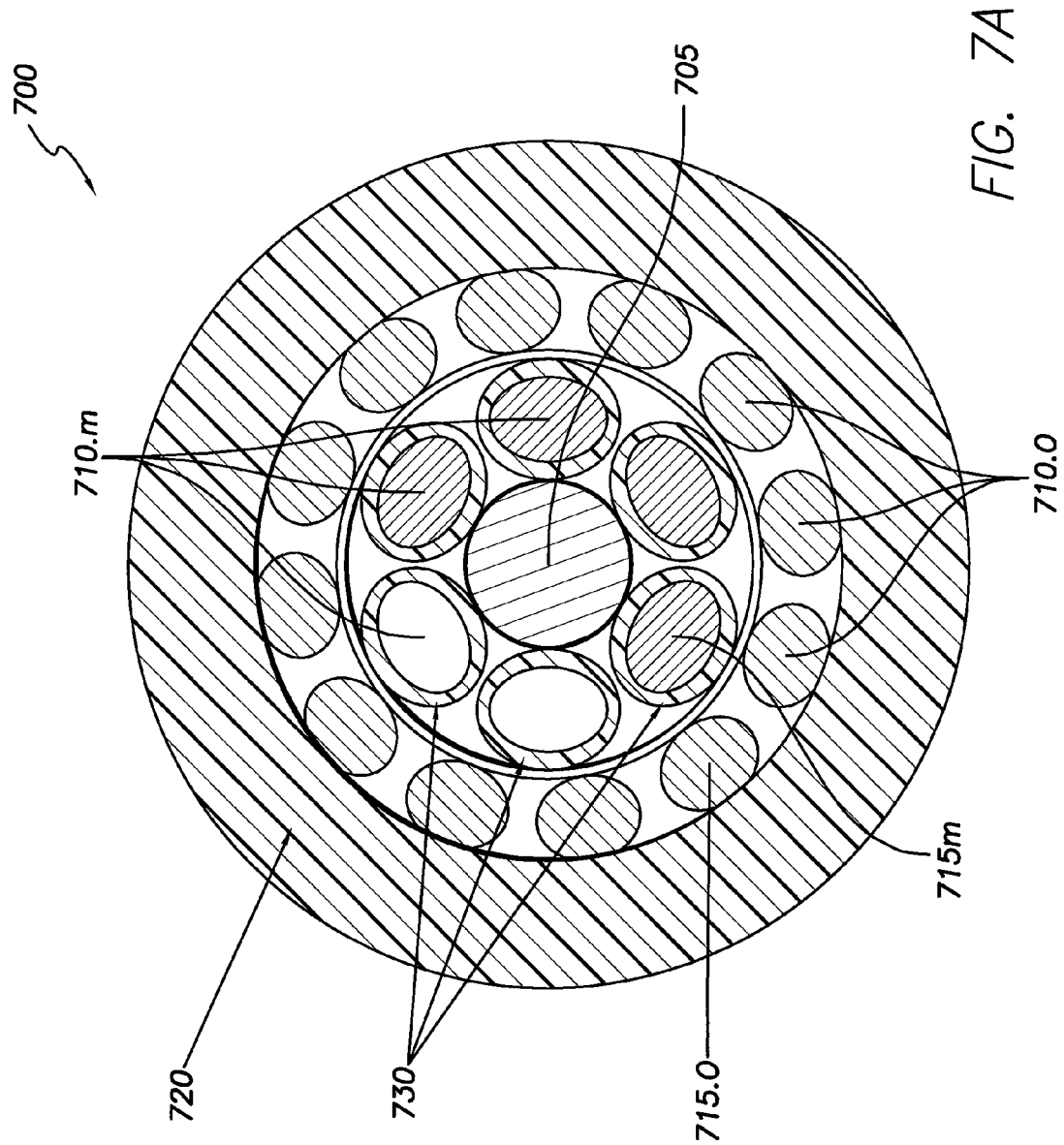
FIG. 7A illustrates another exemplary cable configured for improved mechanical and electrical properties according the present cable and lead designs.

FIG. 7A is an illustration of another embodiment of exemplary cable 700 configured for improved mechanical and electrical properties according to the present cable and lead designs. Cable 700 includes central wire 705, middle cable-layer 710.m, outer cable-layer 710.o, middle filaments 715.m of middle cable-layer 710.m, outer filaments 715.o of outer cable-layer 710.o, cable jacket 720, and filament coatings 725.

Many of the features or elements of exemplary cable 700 are the same or substantially similar to elements of exemplary cable 600 already discussed above in conjunction with FIG. 6. For example, central wire 705 corresponds to central wire 605. Middle cable-layer 710.m is substantially similar to middle cable-layer 610.m. Middle filaments 715.m are substantially similar to middle filaments 615.m, etc. A discussion of these elements, their relative orientation and structural properties and advantages has already been presented above and the discussion will not be repeated here.

Notable, however, with exemplary cable 700 is that rather than central wire coating 625 (see FIG. 6) which is omitted in this configuration, filaments 715.m of middle cable-layer 710.m have individual filament coatings 730. These filament coatings 730 may be comprised of any number of polymers, such as that already enumerated above.

In addition, filament coating 730 serve to reduce fretting fatigue in multiple respects. Filament coatings 730 reduce fretting fatigue between middle filaments 715.m and central wires 705. Filament coating 730 also reduce fretting fatigue due to contact pressure between middle filaments 715.m and outer filaments 715.o. Filament coating 730 also reduce fretting fatigue between filaments 715.m of middle cable-layer 710.m.

Figure 7B:
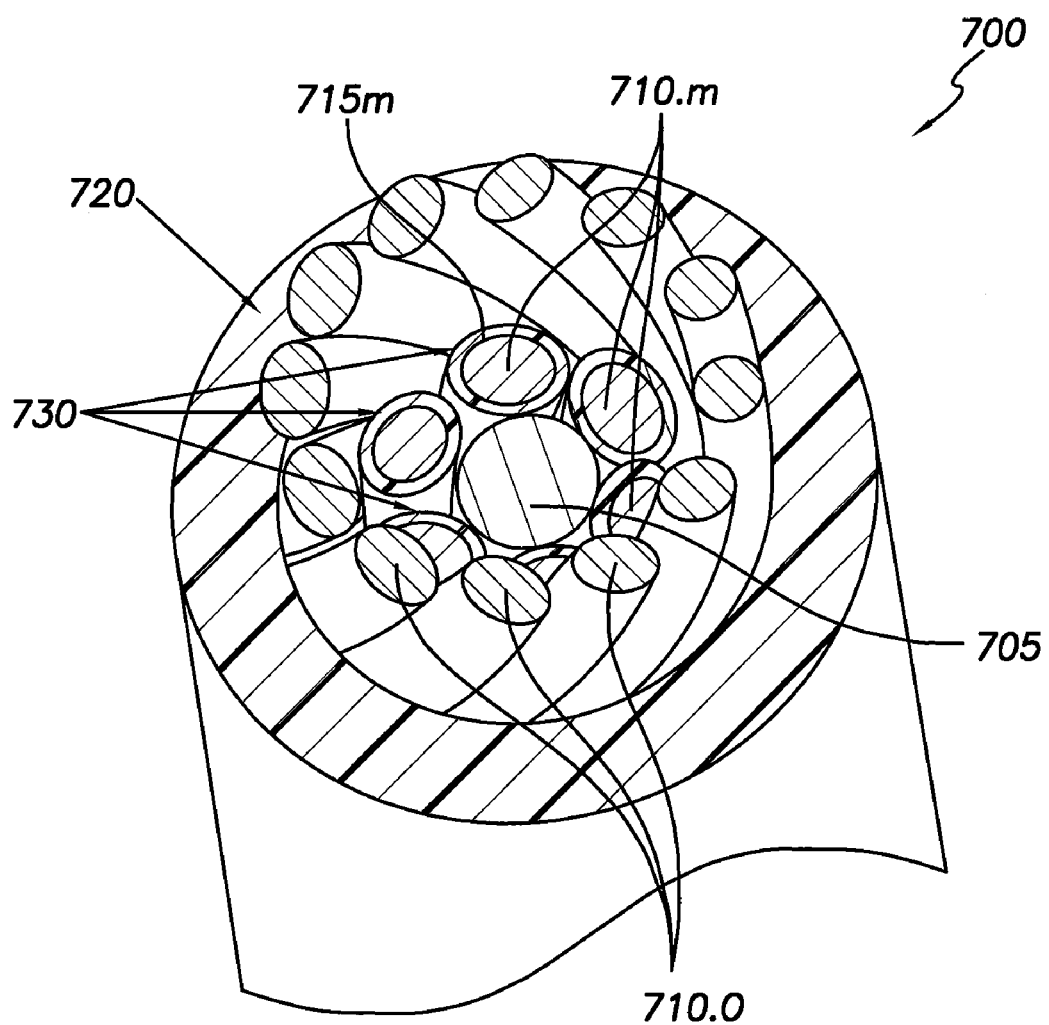
FIG. 7B illustrates another view of the exemplary cable of FIG. 7A.

FIG. 7B is another view of exemplary cable 700 configured for improved mechanical and electrical properties. FIG. 7B shows elements which are substantially the same as the elements shown in cross-sectional view in FIG. 7A. In FIG. 7B a perspective view is offered, making clearer the windings of filaments 715.o and also the overall extension of exemplary cable 700.

Figure 7C:
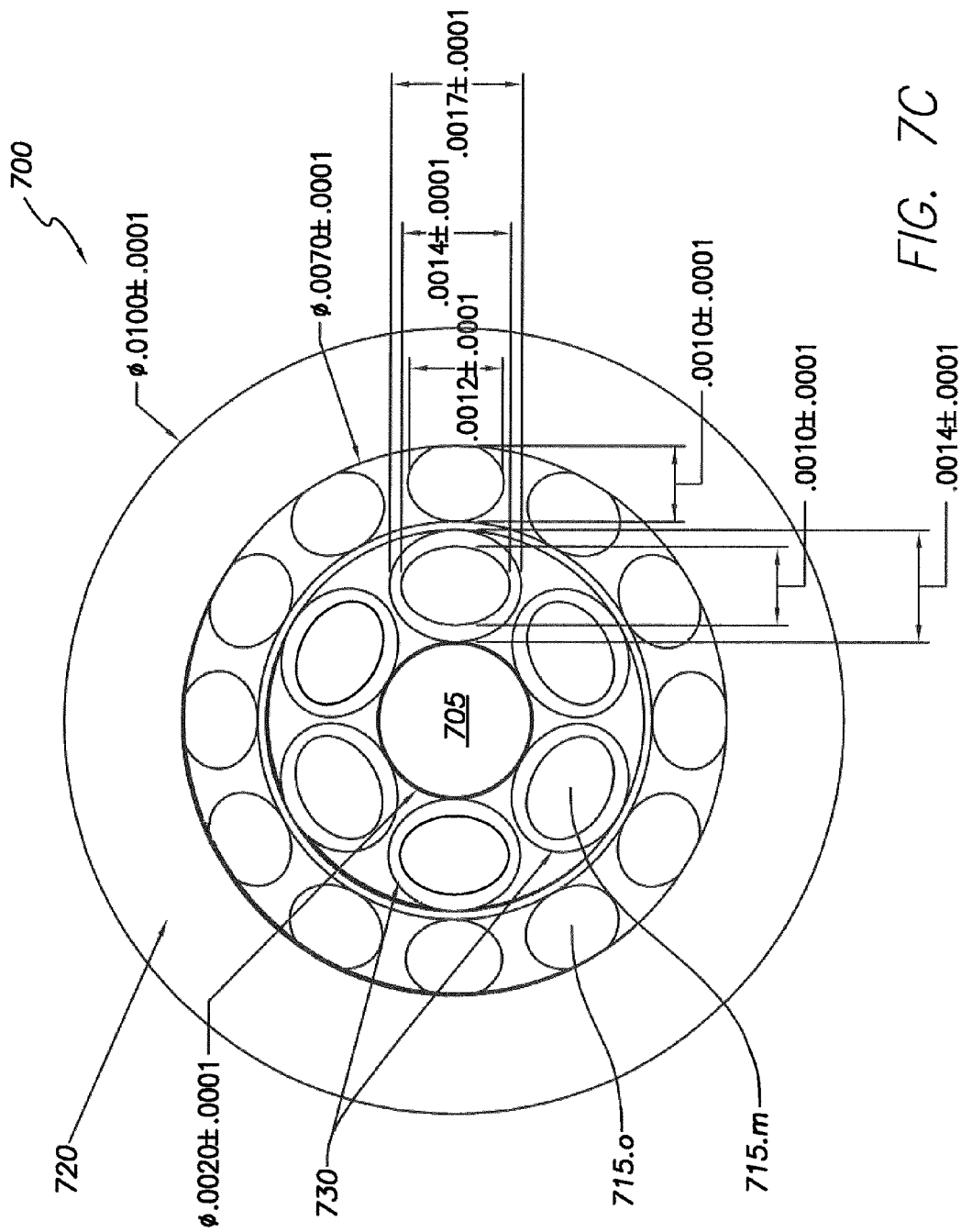
FIG. 7C illustrates another view of the exemplary cable of FIG. 7A.

FIG. 7C offers another cross-sectional view of exemplary cable 700. FIG. 7C includes exemplary measurements of various elements of exemplary cable 700. Persons skilled in the relevant arts will appreciate that the measurements shown here are exemplary only. Other dimensions for various elements may be employed within the spirit and scope of the present cable and lead designs.

Persons skilled in the relevant arts will appreciate that the exact configuration shown for cable 700 is exemplary only, and in implementation may vary in any number of details. More cable-layers 710 or fewer cable-layers may be employed. Similarly, the number of filaments 715 used in each cable-layer is exemplary and may vary in actual implementation. Similarly, the relative sizes of the elements are exemplary only and may vary in actual implementation.

Figure 8A:
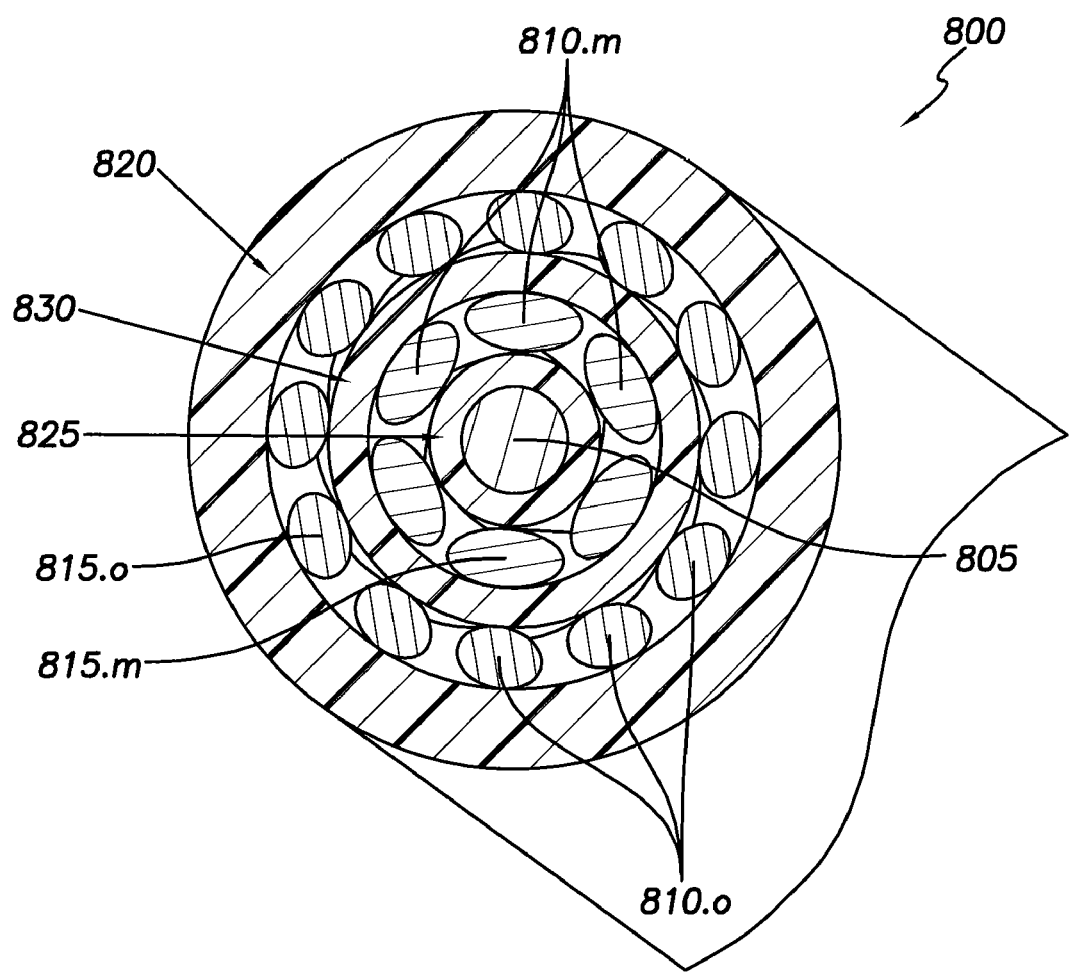
FIG. 8A illustrates another exemplary cable configured for improved mechanical and electrical properties according the present cable and lead designs.

FIG. 8A presents a view of an exemplary cable 800 configured for improved mechanical and electrical properties according to the present cable and lead designs. Elements of exemplary cable 800 include central wire 805, outer cable-layer 810.o, middle cable-layer 810.m, multiple outer oval filaments 815.o of outer cable-layer 810.o, and multiple middle oval filaments 815.m of middle cable-layer 810.m. These elements are the same or substantially similar as corresponding elements already described in conjunction with FIGS. 6-7. For example, central wire 805 corresponds to central wires 705 and 605. Middle cable-layer 810.m is substantially similar to middle cable-layer 710.m and 610.m. Middle filaments 815.m are substantially similar to middle filaments 715.m and 615.m, etc. A discussion of these elements, their relative orientation and structural properties and advantages has already been presented above and the discussion will not be repeated here.

New to exemplary cable 800 is the use of two inner jackets 825 and 830. Central wire coating 825 is similar to central wire coating 625 already discussed above. It helps reduce fretting fatigue between central wire 805 and middle cable-layer 810.m. Inter-middle cable-layer/outer cable-layer coating 830 is similarly configured to reduce fretting fatigue between middle cable-layer 810.m and outer cable-layer 810.o. In addition, exemplary cable 800 has cable jacket 820 which provides installation for the cable as a whole.

Figure 8B:
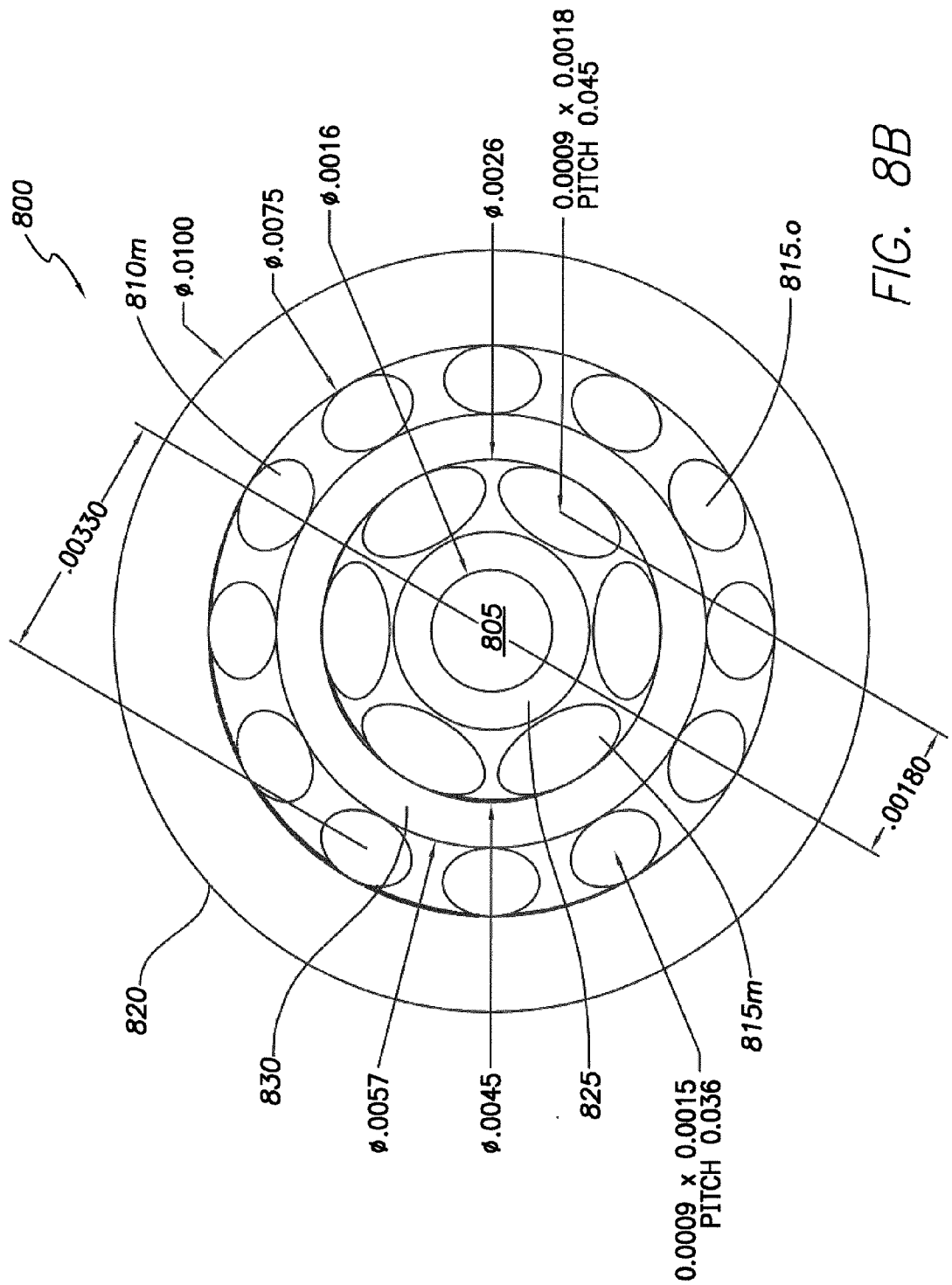
FIG. 8B illustrates another view of the exemplary cable of FIG. 8A.

FIG. 8B presents another view of exemplary cable 800. Presented in FIG. 8B are exemplary measurements for various elements of exemplary cable 800 such as widths, diameters, and pitches for the central wire 805, filaments 815 and coatings 820, 825 and 830. Persons skilled in the relevant arts will appreciate that the measurements shown are exemplary only. Other dimensions may be employed consistent with the spirit and scope of the present cable and lead designs.

Persons skilled in the relevant arts will appreciate that the exact configuration shown for cable 800 is exemplary only, and in implementation may vary in any number of details. More cable-layers 810 or fewer cable-layers may be employed. Similarly, the number of filaments 815 used in each cable-layer is exemplary and may vary in actual implementation. Similarly, the relative sizes of the elements are exemplary only and may vary in actual implementation.

Figure 9A:
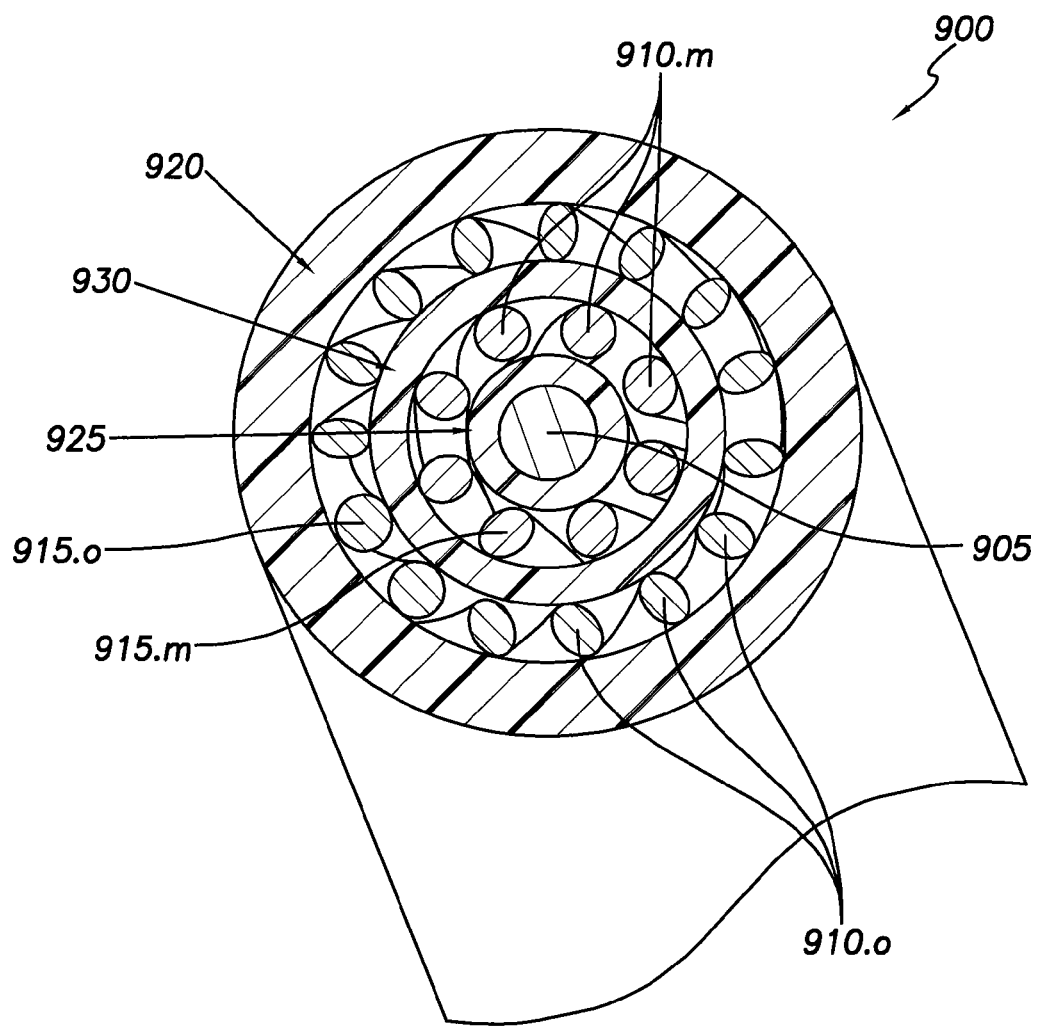
FIG. 9A illustrates another exemplary cable configured for improved mechanical and electrical properties according the present cable and lead designs.

FIG. 9A presents a view of another exemplary cable 900 configured for improved mechanical and electrical properties. FIG. 9A includes a central wire 905, an outer cable-layer 910.o, a middle cable-layer 910.m, filaments 915.o of outer cable-layer 910.o, filaments 915.m of middle cable-layer 910.m, central wire coating 925, and inter-middle cable-layer/outer cable-layer coating 930.

Unlike other embodiments shown above, such as, exemplary cables 600/800, exemplary cable 900 employs conventional filaments 915 with circular cross-sections, rather than the oval cross-sections discussed above for filaments 615/815 with exemplary cables 600/800.

However, exemplary cable 900 still benefits from other advantages of the present cable and lead designs. For example, exemplary cable 900 employs central wire coating 925 and inter-middle cable-layer/outer cable-layer coating 930. Central wire coating 925 reduces fretting fatigue between central wire 905 and middle cable-layer 910.*m*. Similarly, inter-middle cable-layer/outer cable-layer coating 930 reduces fretting fatigue between middle cable-layer 910.*m* and outer cable-layer 910.*o*. As a result of coatings 925 and 930, and the consequent reduction in fretting fatigue, cable reliability is increased. In addition, due to the reduced fretting fatigue between cable-layers 910, and also between middle cable-layer 910.*m* and central wire 905, it is still possible to wind filaments 915 with a stronger helical winding, with the various advantageous to such windings already discussed above.

In addition, while not specifically illustrated in the figure, the metallic composition of the cable-layers may also vary with radial distance from the center, again providing the advantages discussed above. (See FIG. 10 for further discussion.) In addition, it may be seen in the figure that central wire 905 has a greater cross-sectional area than the cross-sectional area of filaments 915.*m* in middle cable-layer 910.*m*. While not illustrated in the figure, in an embodiment filaments 915.*o* of outer cable-layer 910.*o* may have a lesser cross-sectional area than filaments 915.*m* of middle cable-layer 910.*m*.

Figure 9B:
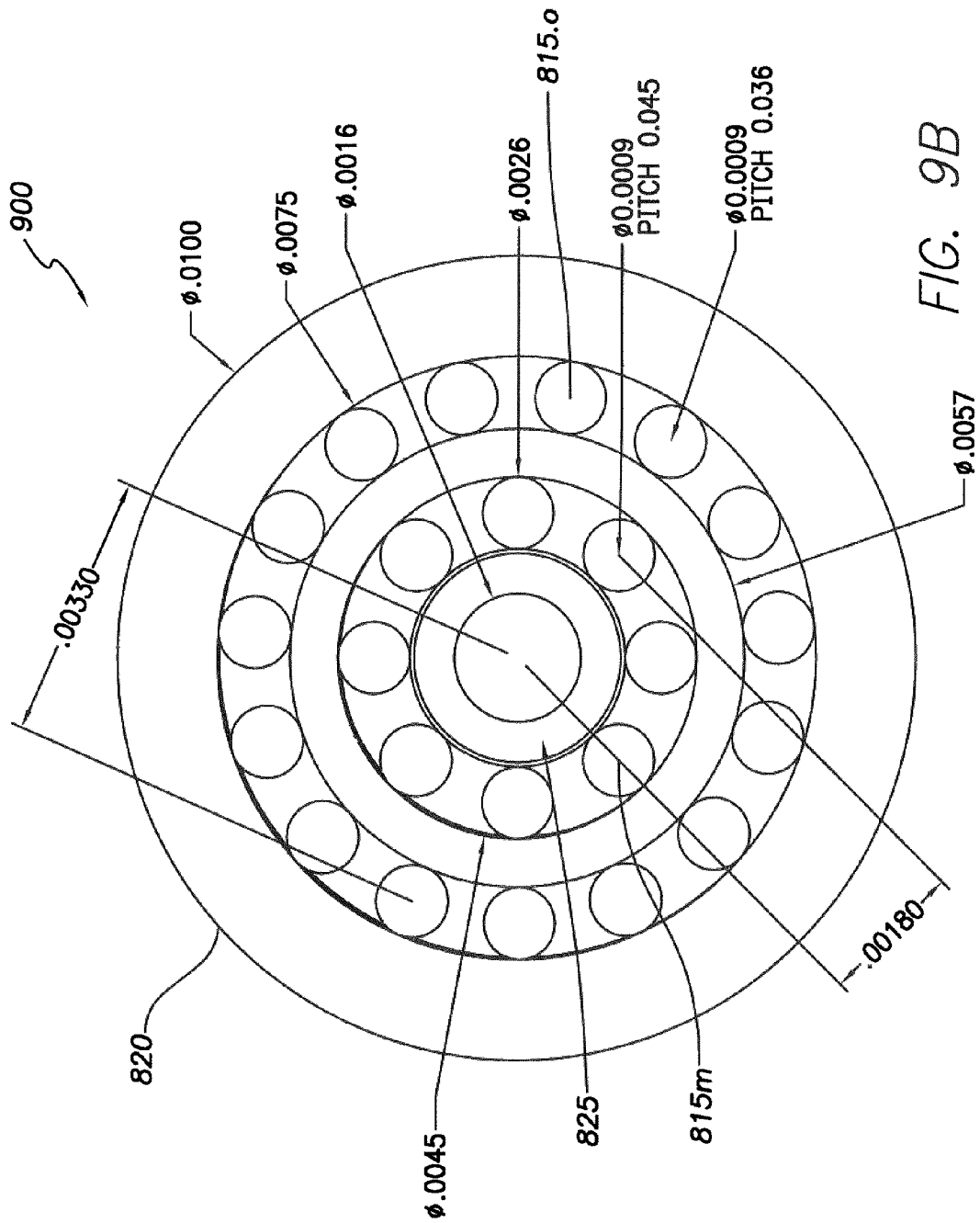
FIG. 9B illustrates another view of the exemplary cable of FIG. 9A.

FIG. 9B is a cross-sectional view of exemplary cable 900 already discussed above. FIG. 9B includes exemplary measurements for various elements for exemplary cable 900. Persons skilled in the relevant arts will appreciate that the measurements shown are exemplary only. Others measurements may be employed consistent with the spirit and scope of the present cable and lead designs.

More generally it will be appreciated that in all the embodiments discussed above, that is exemplary cables 600, 700, 800 and 900 the exact configurations shown are exemplary. The number of cable-layers 910 may be greater or fewer than shown. The number of filaments 915 may be greater or fewer than shown. Configurations of jackets such as 920, 925 and 930 as well as filament coating 730 may be combined or varied in different combinations. Other elements may be added or removed consistent with the spirit and scope of the present cable and lead designs. Further, in embodiments shown above the central wire 605, 705, 805 and 905 has been illustrated as being a single filament generally of larger cross-sectional area than any of the filaments in the surrounding cable-layers 910. Persons skilled in the relevant arts will appreciate that the central filament itself may be composed either of a single filament 915 of a same cross-sectional area as a filament 915 in a surrounding cable-layer. In alternative embodiments, central wire 905 may actually be composed of multiple filaments 915 which may be braided, wound together, or otherwise combined or coupled to constitute a functional central wire 905.

Material Composition of Central Wire and Filaments

Central wire 605/905 and filaments 615/915 employed in exemplary cables 600/900, as well as other filaments consistent with the present cable and lead designs, may be comprised of a variety of conducting materials, including for example and without limitation such metals as silver, copper, nickel, chromium, aluminum, iron, molybdenum, tin, platinum, gold, cobalt, tungsten, etc., and alloys of such metals.

In an embodiment, central wire 605/905 and filaments 615/915 are constructed as drawn filled tube (DFT) wires having a drawn outer tube filled with an inner core material. In an embodiment, the outer tube of each filament may be comprised of the alloy MP35N® (an alloy composed of approximately 35% cobalt, approximately 35% nickel, approximately 20% chromium, and approximately 10% molybdenum, along with small or trace quantities of other elements), MP35N is a trademark of SPS Technologies, Inc., of Jenkintown, Pa. In an embodiment, the inner core of each filament may be comprised of high purity silver (Ag).

Figure 10:
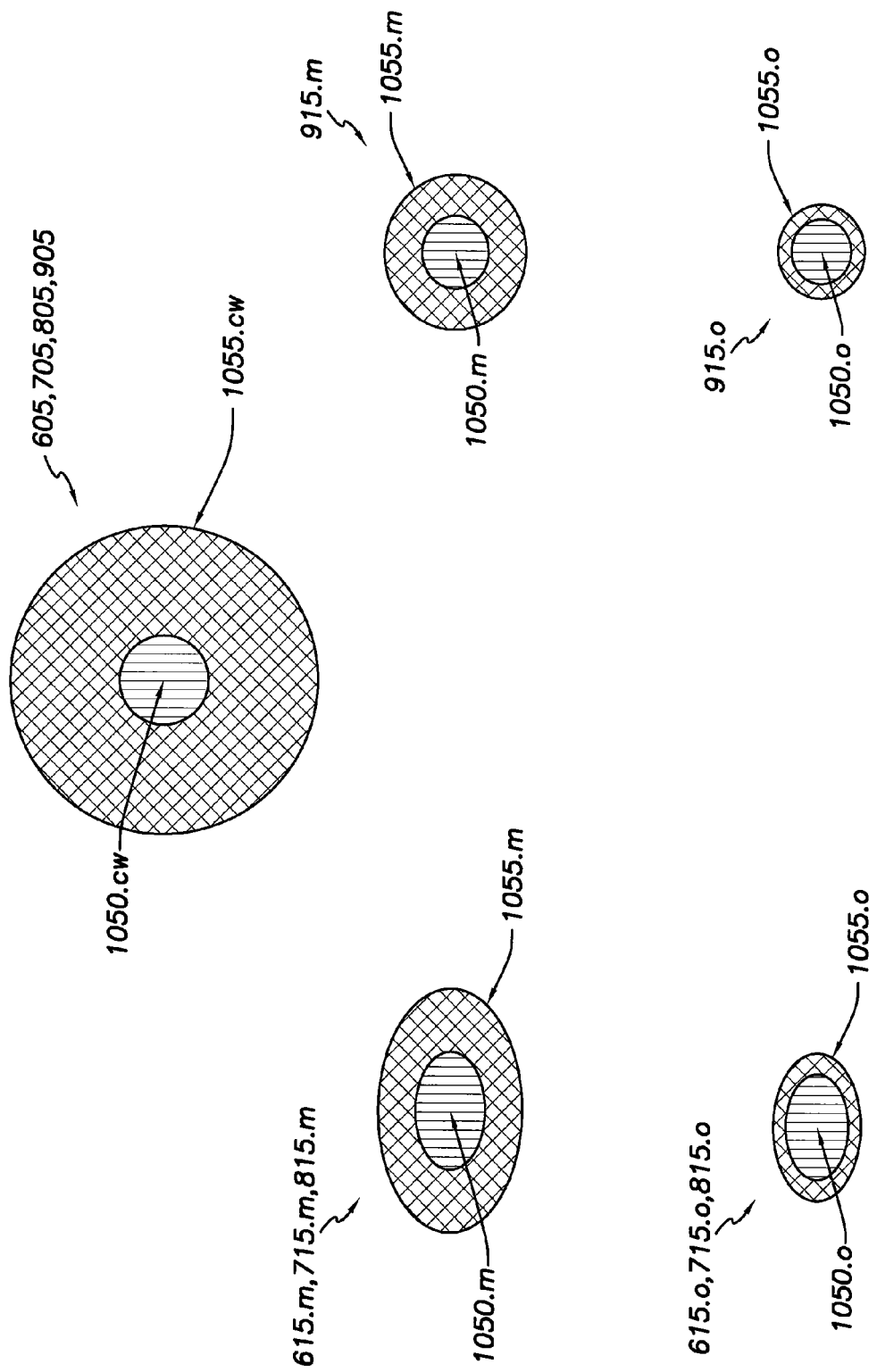
FIG. 10 illustrates cross-sectional views of several exemplary filaments which may be part of a cable configured for improved mechanical and electrical properties according the present cable and lead designs.

FIG. 10 illustrates cross-section view of several exemplary filaments 615/915 according to the present cable and lead designs. Each filament 615/915 has an exterior outer tubing 1055 which, as discussed immediately above, may be comprised of the alloy MP35N. Each filament also has a core 1050 running down the center and comprised of high purity silver.

As per discussion above, the cross-sectional area of a filament 615/915 may decrease with increasing distance from the center of cable 600/900. As shown in FIG. 10, central wire 605/905 has a larger cross-sectional area than middle filaments 615.*m*/915.*m*. Similarly, middle filaments 615.*m*/915.*m* have a larger cross-sectional area than outer filaments 615.*o*/915.*o*. Also consistent with the discussion above associated with FIGS. 6A-9B, filaments 615.*m*/815.*m*, 615.*o*/815.*o* are illustrated as substantially oval in cross-section, while filaments 915.*m* and 915.*o* are presented as substantially circular in cross-section.

In addition, in an embodiment of the present cable and lead designs, the percentage of silver in a filament, as a percentage of the total volume of the filament, may also vary with increasing distance from the center of a cable 600/900. This change in silver percentage will also be reflected in a change in the cross-sectional area of a filament which is silver, as compared with the percentage of the cross-sectional area which is an alloy such as MP35N.

For example, for central wires 605/905, silver core 1050.*cw* may be approximately 20% to 30% of the total volume and cross-sectional area of the filament, with alloy tube 1055.*cw* comprising the remaining 80% to 70% by volume and cross-sectional area. In an embodiment, a central wire 605/905 may have a silver core 1050.*cw* which comprises approximately 28% of the wire.

For middle filaments 615.*m*/915.*m*, silver core 1050.*m* may be approximately 30 to 40% of the total volume and cross-sectional area of the filaments, with alloy tube 1055.*m* comprising the remaining 70% to 60% by volume and cross-sectional area. In an embodiment, a middle filament 615.*m*, 715.*m*, 815.*m*, 915.*m* may have a silver core 1050.*m* which comprises approximately 33% of the wire.

For outer filaments 615.*o*/915.*o*, silver core 1050.*o* may be approximately 40 to 60% of the total volume and cross-sectional area of the filament, with alloy tube 1055.*o* comprising the remaining 60% to 40% by volume and cross-sectional area. In an embodiment, an outer filament 615.*o*/915.*o* may have a silver core 1050.*o* which comprises approximately 41% of the wire.

It should be noted that any central wire coating, such as exemplary central wire coatings 625, 825, and 925 shown in various of FIGS. 6, 8, and 9 above, or filament coatings, such as exemplary coatings 730 shown in FIGS. 7, are not illustrated in FIG. 10. But, such coatings 625, 825, 925, 730, if used, would be exterior to, jacketing, and in contact with alloy tube 1055.

It should be further noted that elements of FIG. 10 are intended to illustrate relative dimensions, such as for example the relative percentages of silver compared with alloy in a central wire, a middle filament, and an outer filament, without necessarily being drawn exactly to scale. It will also be understand by persons skilled in the relevant arts that the relative percentages of core metal 1050 compared with tube metal 1055 may vary from that described above. In particular, in embodiments with only one layer of cable-layer 910 surrounding central wire 905, or with three or more layers of cable-layers 910 surrounding central wire 905, the percentages of silver in successive cable-layer(s) may vary from that described above.

In an embodiment, the percentage of silver in the core 1050 as compared with the percentage of alloy in the filament tube 1055 will progressively increase in filaments 615/915 working outwards from the central wire 605/905, through one or more middle cable-layers 610.*m*/910.*m*, towards an outermost cable-layer 610.*o*/910.*o*.

It should also be noted that the choice of silver for filament core 1050 and MP35N for tube 1055 is exemplary only. In alternative embodiments, other metals and/or alloys may be employed for core 1050, and other metals and/or alloys may be employed for tube 1055. Depending on the choice of material for core 1050 and tube 1055, the percentage of core material 1050 may decrease (rather than increase) working outwards from the central wire 605/905 towards an outermost cable-layer 610/910.

As already described above, the choice of both materials for filament core material 1050 and filament tube 1055, as well as the relative percentages allocated between core 1050 and tube 1055, is generally selected such that the strength of the materials decreases from the center wire 605/905 to one or more middle layers 610.*m*/910.*m* to the outer layer 610.*o*/910.*o*, such that cable 600/900 as a whole will offer higher tensile strength but less flex/bending stiffness. Materials and relative percentages will also be chosen with a view towards reducing DC resistance and optimizing MRI compatibility, as already described above.

Alternative Embodiments

Described above have been a number of exemplary embodiments 600/900 of cable conductors configured for improved mechanical and electrical performance in implantable biomedical leads. Referring again to FIGS. 6-10, such cables have comprised a central wire 605/905, cable layers 610/910, filaments 615/915 of the cable layers 610/910, and various coatings and jackets 620, 625, 720, 730, 820, 825, 920, 925, 930. Other elements, not shown or discussed, may be included as well, consistent with the present cable and lead designs.

Figure 11:
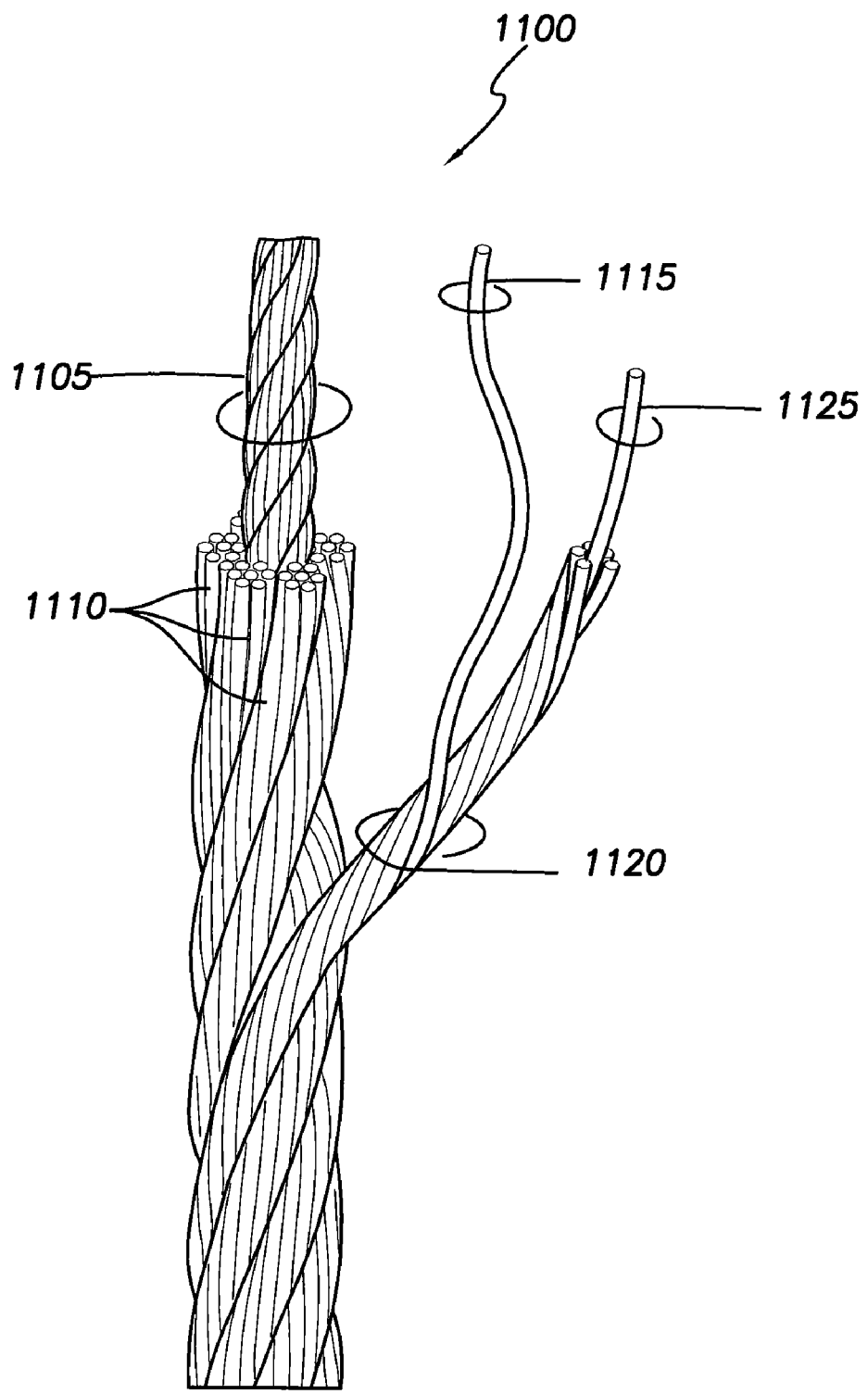
FIG. 11 illustrates an exemplary rope cable.

Persons skilled in the relevant arts will appreciate that conducting cables may be designed and configured with various elements, such as wires 605/905, filaments 615/915, and other elements combined in a manner different than that illustrated and described above in FIGS. 6-10. FIG. 11, for example, illustrates an exemplary cable 1100 which, using terminology sometimes employed in the art, may be known as a rope cable 1100.

Rope cable 1100 may employ a plurality of strands 1120, where each strand may be comprised of multiple strand filaments 1115 which are wrapped or twisted together in a spiral or helical fashion, or otherwise coupled to each other. Strand filaments 1115 may, for example, be wrapped in spiral or helical fashion around a central strand filament 1125. In turn, and as illustrated in FIG. 11, the plurality of strands 1120 may be wrapped in spiral or helical fashion around a rope core 1105 to form a rope layer 1110. While not shown in the figure, additional rope layers 1110 may be employed, each layer 1110 surrounding a layer 1110 interior to itself. The plurality of strands 1120 may also be bonded, coupled, or joined in some other fashion. Rope core 1105 may be a single, unitary wire, or may itself be comprised of multiple filaments conjoined or coupled in various manners.

While not shown in rope cable 1100 of FIG. 11, persons skilled in the relevant arts will recognize that the elements, systems, and methods disclosed elsewhere herein, in conjunction with other embodiments of the present cable and lead designs, may be advantageously employed in other embodiments, for example in rope cable 1100. For example, strand filaments 1115 could be configured to have oval cross-sections, and the oval cross-sections oriented to maximize a contact area between strand filaments 1115 and central filament 1125, or to maximize a contact area between strand filaments 1115 and surrounding strand filaments of a second strand layer (not illustrated), with the advantages already described above.

Similarly, various types of polymer jackets could be employed around strand filaments 1115, ropes 1120, rope core 1105, rope layer(s) 1110, and/or central strand filament 1125 and/or elements thereof to reduce fretting fatigue between these elements. Similarly, the composition, for example (ratios of metals employed in construction) of strand filaments 1115 and/or central strand filament 1125 may be varied depending on radial distance from a central locus or based on other geometric or structural considerations, with the advantages already described above. Similarly, the cross-sectional area of strand filaments 1115, central strand filament 1125, and strands 1120 may be varied with radial distance from a central locus or based on other geometric or structural considerations, with the advantages already described above.

More generally, persons skilled in the relevant arts will recognize that the elements disclosed herein may be combined in a variety of manners, in conducting cables of various configurations, to achieve some or all of the advantages described herein.

CONCLUSION

It is to be appreciated that the Detailed Description section, and not the Summary and Abstract sections, is intended to be used to interpret the claims. The Summary and Abstract sections may set forth one or more but not all exemplary embodiments of the present cable and lead designs as contemplated by the inventor(s), and thus, are not intended to limit the present apparatus and method and the appended claims in any way.

Moreover, while various embodiments of the present cable and lead designs have been described above, it should be understood that they have been presented by way of example, and not limitation. It will be apparent to persons skilled in the relevant art(s) that various changes in form and detail can be made therein without departing from the spirit and scope of the present cable and lead designs. Thus, the present cable and lead designs should not be limited by any of the above described exemplary embodiments, but should be defined only in accordance with the following claims and their equivalents.

In addition, it should be understood that the figures, which highlight the functionality and advantages of the present cable and lead designs, are presented for example purposes only. The architecture of the present cable and lead designs is sufficiently flexible and configurable, such that it may be constructed and utilized in ways other than that shown in the accompanying figures. Moreover, the steps, processes, methods, and/or construction techniques indicated in the exemplary system(s) and method(s) described above may in some cases be performed in a different order, or by combining elements in a different manner, than the order or manner described, and some steps may be added, modified, or removed, without departing from the spirit and scope of the present cable and lead designs.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present cable and lead designs in any way.

What is claimed is:

1. A cable comprising:
   a conductive central core; and
   at least one conductive cable-layer concentric with the central core and surrounding at least one of the conductive central core and a conductive cable-layer interior to itself;
   wherein:
   each at least one conductive cable-layer is comprised of a plurality of conductive filaments, said filaments configured to provide an elongated contact area between the at least one conductive cable-layer and either the conductive central core or a second conductive cable-layer immediately interior to the at least one conductive cable-layer.

2. The cable of claim 1, wherein a conductive filament of the at least one conductive cable-layer has a substantially oval cross section.

3. The cable of claim 2, wherein:
   the elongated contact area of the substantially oval cross section conductive filament is substantially parallel to a longer cross-sectional axis of the filament; and
   the elongated contact area of the substantially oval cross section conductive filament is oriented such that the elongated contact area makes contact with at least one of the conductive central core or the second conductive cable-layer;
   wherein the substantially oval cross section conductive filament is configured to maximize a contact area between the at least one conductive cable-layer and at least one of the conductive central core or the second conductive cable-layer.

4. The cable of claim 1, wherein the cross sectional area of a filament of the plurality of conductive filaments progressively decreases with an increasing radial distance from the conductive central core, wherein:
   the conductive central core has a cross sectional area that is greater than a cross sectional area of a filament in the cable-layers; and
   each filament of a first cable-layer of the at least one conductive cable-layers has a cross-sectional area that is greater than a cross sectional area of a filament of a cable-layer exterior to the first cable-layer.

5. The cable of claim 1, wherein the material composition of a filament progressively changes with an increasing radial distance from the conductive central core, the material composition determining a material strength of the filament, wherein:
   the conductive central core has a material strength that is greater than a material strength of each filament in the cable-layers; and
   each filament of a first cable-layer of the one or more cable-layers has a material strength that is greater than a material strength of a filament of a cable-layer exterior to the first cable-layer.

6. The cable of claim 5, wherein:
   the conductive central core and each filament of the at least one conductive cable-layer comprises an inner silver core and an outer alloy;
   the conductive central core has a lower percentage silver content of its inner silver core than a percentage silver content of the inner cores of the filaments in the at least one conductive cable-layer; and
   each filament of a first conductive cable-layer of the at least one conductive cable-layer has a lower percentage silver content of its inner silver core than percentage silver content of an inner core of a filament of a conductive cable-layer exterior to the first conductive cable-layer.

7. The cable of claim 6, wherein:
   the conductive central core has a silver content in a range of approximately 20% to 30%;
   each conductive filament of a first conductive cable-layer immediately surrounding the conductive central core has a silver content in a range of approximately 30% to 40%; and
   each conductive filament of a second conductive cable-layer immediately surrounding the first conductive cable-layer has a silver content in a range of approximately 40% to 60%.

8. The cable of claim 1, further comprising a non-conductive coating between at least one of:
   the conductive central core and a conductive cable-layer immediately surrounding the conductive central core; or
   a first conductive cable-layer of the at least one conductive cable-layer and an immediately adjacent second cable-layer of the at least one conductive cable-layer;
   wherein:
   the non-conductive coating is configured to reduce a fretting fatigue at the elongated contact area while mediating and maintaining the elongated contact area.

9. The cable of claim 1, further comprising a non-conductive coating jacketing each filament of a least one cable-layer of the at least one conductive cable-layer, wherein the non-conductive coating is configured to minimize at least one of:
   a fretting at the area of contact between the cable-layer and either the conductive central core or a cable-layer immediately adjacent to itself; and
   a fretting fatigue at the area of contact between the plurality of filaments of the cable-layer.

10. A lead comprising:
    an extended exterior insulating body having a lumen; and
    a cable disposed within said lumen, said cable comprising:
    a conductive central core; and
    at least one conductive cable-layer concentric with the central core and surrounding at least one of the conductive central core and a conductive cable-layer interior to itself;
    wherein:
    each at least one conductive cable-layer is comprised of a plurality of conductive filaments, said filaments configured to provide an elongated contact area between the at least one conductive cable-layer and either the conductive central core or a second conductive cable-layer immediately interior to the at least one conductive cable-layer.

11. The lead of claim 10, wherein:
    a conductive filament of the at least one conductive cable-layer has a substantially oval cross section; and
    the elongated contact area of the substantially oval cross section conductive filament is substantially parallel to a longer cross-sectional axis of the filament; and
    the elongated contact area of the substantially oval cross section conductive filament is oriented such that the elongated contact area makes contact with at least one of the conductive central core or the second conductive cable-layer;
    wherein the substantially oval cross section conductive filament is configured to maximize a contact area between the at least one conductive cable-layer and at least one of the conductive central core or the second conductive cable-layer.

12. The lead of claim 10, wherein the cross sectional area of a filament progressively decreases with an increasing radial distance from the conductive central core, wherein:
    the conductive central core has a cross sectional area which is greater than a cross-sectional area of each filament in the cable-layers; and each filament of a first cable-layer of the at least one conductive cable-layer has a cross-sectional area which is greater than a cross-sectional area of a filament of a cable-layer exterior to the first cable-layer.

13. The lead of claim 10, wherein the material composition of a filament progressively changes with an increasing radial distance from the conductive central core, the material composition determining a material strength of the filament, wherein:
the conductive central core has a material strength which is greater than a material strength of each filament in the cable-layers; and
each filament of a first cable-layer of the one or more cable-layers has a material strength which is greater than a material strength of a filament of a cable-layer exterior to the first cable-layer.

14. The lead of claim 10, further comprising a non-conductive coating between at least one of:
the conductive central core and the cable-layer immediately surrounding the conductive central core; or
a first cable-layer and an immediately adjacent second cable-layer of the at least one conductive cable-layer;
wherein:
the non-conductive coating is configured to minimize a fretting fatigue.

15. The lead of claim 10, further comprising a non-conductive coating jacketing each filament of a least one cable-layer of the at least one conductive cable-layer, wherein the non-conductive coating is configured to minimize at least one of:
a fretting fatigue at the area of contact between the cable-layer and either the conductive central core or a cable-layer immediately adjacent to itself; and
a fretting fatigue at the area of contact between the plurality of filaments of the cable-layer.

16. An implantable system for delivery of cardiac therapy comprising:
an implantable cardiac therapy device (ICTD); and
a lead configured to be connected at a proximal end to said ICTD and configured to be attached at a distal end to a tissue of a patient;
wherein said lead comprises:
an extended exterior insulating body having a lumen; and
a cable situated within said lumen, said cable comprising:
a conductive central core; and
at least one conductive cable-layer concentric with the central core and surrounding at least one of the conductive central core and a conductive cable-layer interior to itself;
wherein:
each at least one conductive cable-layer is comprised of a plurality of conductive filaments, said filaments configured to provide an elongated contact area between the at least one conductive cable-layer and either the conductive central core or a second conductive cable-layer immediately interior to the at least one conductive cable-layer.

17. A cable, comprising:
a conductive central core;
at least one conductive cable-layer concentric with the central core and surrounding at least one of the conductive central core and a conductive cable-layer interior to itself; and
a plurality of conductive filaments of the at least one conductive cable-layer;
wherein:
the cross sectional area of a filament of the plurality of conductive filaments progressively decreases with an increasing radial distance from the conductive central core, wherein:
the conductive central core has a cross sectional area which is greater than a cross-sectional area of a filament in the cable-layers; and
each filament of a first cable-layer of the at least one conductive cable-layers has a cross-sectional area which is greater than a cross-sectional area of a filament of a cable-layer exterior to the first cable-layer;
and;
the material composition of a filament progressively changes with an increasing radial distance from the conductive central core, the material composition determining a material strength of the filament, wherein:
the conductive central core has a material strength which is greater than a material strength of a filament in the cable-layers; and
each filament of a first cable-layer of the one or more cable-layers has a material strength which is greater than a material strength of a filament of a cable-layer exterior to the first cable-layer.

18. The cable of claim 17, wherein a conductive filament of the at least one conductive cable-layer has a substantially oval cross section, wherein:
an elongated surface contact area of the substantially oval cross section conductive filament is oriented such that the surface elongated contact area makes contact pressure with at least one of the conductive central core or the second conductive cable-layer.

19. The cable of claim 17, wherein:
the conductive central core and each filament of the at least one conductive cable-layer comprises an inner silver core and an outer alloy surrounding the inner silver core;
the conductive central core has a percentage silver content of its inner silver core which is less than a percentage silver content of a filament in the at least one conductive cable-layer; and
each filament of a first conductive cable-layer of the at least one conductive cable-layer has a percentage silver content of its inner silver core which is less than a percentage silver content of a filament of a conductive cable-layer exterior to the first conductive cable-layer.

20. The cable of claim 17, further comprising a non-conductive coating between at least one of:
the conductive central core and a conductive cable-layer immediately surrounding the conductive central core;
a first conductive cable-layer of the at least one conductive cable-layer and an immediately adjacent second cable-layer of the at least one conductive cable-layer;
wherein:
the non-conductive coating is configured to reduce a fretting fatigue at the area of contact while mediating and maintaining the elongated contact area.

21. The cable of claim 17, further comprising a non-conductive coating jacketing each filament of a least one cable-layer of the at least one conductive cable-layer, wherein the non-conductive coating is configured to minimize at least one of:
a fretting fatigue between the cable-layer and either the conductive central core or a cable-layer immediately adjacent to itself; and
a fretting fatigue between the plurality of filaments of the cable-layer.

* * * * *